(12) United States Patent
Corbo et al.

(10) Patent No.: US 10,047,130 B2
(45) Date of Patent: Aug. 14, 2018

(54) METHODS AND COMPOSITIONS FOR RED-SHIFTED CHROMOPHORE SUBSTITUTION FOR OPTOGENETIC APPLICATIONS

(71) Applicant: Washington University, St. Louis, MO (US)

(72) Inventors: Joseph C. Corbo, St. Louis, MO (US); Jennifer Enright, St. Louis, MO (US); Matthew Toomey, St. Louis, MO (US)

(73) Assignee: WASHINGTON UNIVERSITY, Saint Louis, MO (US)

( * ) Notice: Subject to any disclaimer, the term of this patent is extended or adjusted under 35 U.S.C. 154(b) by 0 days.

(21) Appl. No.: 15/127,337

(22) PCT Filed: Mar. 18, 2015

(86) PCT No.: PCT/US2015/021153
§ 371 (c)(1),
(2) Date: Sep. 19, 2016

(87) PCT Pub. No.: WO2015/142984
PCT Pub. Date: Sep. 24, 2015

(65) Prior Publication Data
US 2017/0183385 A1      Jun. 29, 2017

Related U.S. Application Data

(60) Provisional application No. 61/955,074, filed on Mar. 18, 2014, provisional application No. 62/014,289, filed on Jun. 19, 2014.

(51) Int. Cl.
| | | |
|---|---|---|
| *C12N 15/00* | (2006.01) | |
| *C07K 14/405* | (2006.01) | |
| *A61K 48/00* | (2006.01) | |
| *C12N 15/86* | (2006.01) | |
| *C12N 9/02* | (2006.01) | |

(52) U.S. Cl.
CPC ............ *C07K 14/405* (2013.01); *A61K 48/00* (2013.01); *C12N 9/0008* (2013.01); *C12N 9/0071* (2013.01); *C12N 15/86* (2013.01); *C12Y 102/01036* (2013.01); *C07K 2319/50* (2013.01); *C12N 2750/14143* (2013.01)

(58) Field of Classification Search
None
See application file for complete search history.

(56) References Cited

U.S. PATENT DOCUMENTS

| | | |
|---|---|---|
| 2010/0015095 A1 | 1/2010 | Pan et al. |
| 2013/0066047 A1 | 3/2013 | Spudich et al. |
| 2013/0281379 A1 | 10/2013 | Bamberg et al. |

FOREIGN PATENT DOCUMENTS

| | | |
|---|---|---|
| WO | 199513365 A1 | 5/1995 |
| WO | 199513392 A1 | 5/1995 |
| WO | 199617947 A1 | 6/1996 |
| WO | 199706243 A1 | 2/1997 |
| WO | 199708298 A1 | 3/1997 |
| WO | 199709441 A2 | 3/1997 |
| WO | 199721825 A1 | 6/1997 |
| WO | 199911764 A2 | 3/1999 |
| WO | 2015142984 A1 | 9/2015 |

OTHER PUBLICATIONS

Francis, Transl Vis SCi Technol 2013;2:4,1-15.*
Klapper et al. Front Sys Neurosci 2016;10:Art 74, pp. 1-14.*
Altschul, S. et al., "Gapped BLAST and PSI-BLAST: a new generation of protein database search programs," Nucl. Acid Res., 1997, pp. 3389-3402, vol. 25, No. 17, Oxford University Press.
Bourin, M. et al., "The mouse light/dark box test," Eur. J. Pharmacol., 2003, pp. 55-65, vol. 463, Elsevier Science B.V.
Karlin, S. et al., "Applications and statistics for multiple high-scoring segments in molecular sequences," PNAS, Jun. 1993, pp. 5873-5877, vol. 90.
McLaughlin, S. et al., "Adeno-Associated Virus General Transduction Vectors: Analysis of Proviral Structures," J. Virol., Jun. 1988, pp. 1963-1973, vol. 62, No. 6, American Society for Microbiology.
Montana, C. et al., "Transcriptional Regulation of Neural Retina Leucine Zipper (Nrl), a Photoreceptor Cell Fate Determinant," J. Biol. Chem., Oct. 21, 2011, pp. 36921-36931, vol. 286, No. 42.
Montana, C. et al., "Reprogramming of adult rod photoreceptors prevents retinal degeneration," PNAS, Jan. 29, 2013, pp. 1732-1737, vol. 110, No. 5.
Muller, O. et al., "Random peptide libraries displayed on adeno-associated virus to select for targeted gene therapy vectors," Nat. Biotechnol., Sep. 2003, pp. 1040-1046, vol. 21, No. 9.
Pacak, C. et al., "Recombinant Adeno-Associated Virus Serotype 9 Leads to Preferential Cardiac Transduction In Vivo," Circ. Res., 2006, pp. e3-e9, vol. 99, American Heart Association, Dallas, Texas.
Penaud-Budloo, M. et al., "Adeno-Associated Virus Vector Genomes Persist as Episomal Chromatin in Primate Muscle," J. Virol., Aug. 2008, pp. 7875-7885, vol. 82, No. 16, American Society for Microbiology.
Petrs-Silva, H. et al., "High-efficiency Transduction of the Mouse Retina by Tyrosine-mutant AAV Serotype Vectors," Mol. Ther., Mar. 2009, pp. 463-471, vol. 17, No. 3.
Prigge, M. et al., "Color-tuned Channelrhodopsins for Multiwavelength Optogenetics," J. Biol. Chem., Sep. 14, 2012, pp. 31804-31812, vol. 287, No. 38, The American Society for Biochemistry and Molecular Biology, Inc., USA.

(Continued)

*Primary Examiner* — Qian Janice Li
(74) *Attorney, Agent, or Firm* — Polsinelli PC

(57) ABSTRACT

The present disclosure provides compositions and methods used for optogenetics, wherein the composition comprises an optogenetic device and a retinoid processing enzyme.

6 Claims, 18 Drawing Sheets

(13 of 18 Drawing Sheet(s) Filed in Color)

(56) References Cited

OTHER PUBLICATIONS

Reuter, T. et al., "Rhodopsin and Porphyropsin Fields in the Adult Bullfrog Retina," J. General Physiol., Oct. 1971, pp. 351-371, vol. 58, No. 4.
Romero, P. et al., "Exploring protein fitness landscapes by directed evolution," NIH Public Access Author Manuscript, available in PMC Dec. 6, 2010, pp. 1-25, Published in final edited form as: Nat. Rev. Mol. Cell Biol., Dec. 2009, pp. 866-876, vol. 10, No. 12.
Sahel, J-A et al., "Gene Therapy for Blindness," Annu. Rev. Neurosci., Jul. 8, 2013, pp. 467-488, vol. 36.
Samulski, R. et al., "Cloning of adeno-associated virus into pBR322: Rescue of intact virus from the recombinant plasmid in human cells," PNAS, Mar. 1982, pp. 2077-2081, vol. 79, No. 6.
Samulski, R. et al., "Helper-Free Stocks of Recombinant Adeno-Associated Viruses: Normal Integration Does Not Require Viral Gene Expression," J. Viral., Sep. 1989, pp. 3822-3828, vol. 63, No. 9, American Society for Microbiology.
Senapathy, P. et al., "Molecular Cloning of Adeno-associated Virus Variant Genomes and Generation of Infectious Virus by Recombination in Mammalian Cells," J. Biol. Chem., Apr. 10, 1984, pp. 4661-4666, vol. 259, No. 7.
Sineshchekov, O. et al., "Enhancement of Long-Wavelength Sensitivity of Optogenetic Microbial Rhodopsins by 3,4-Dehydroretinal," NIH Public Access Author Manuscript, available in PMC Jun. 5, 2013, pp. 1-20, Published in final edited form as: Biochem., Jun. 5, 2012, pp. 4499-4506, vol. 51, No. 22.
Snodderly, D. et al., "The Macular Pigment. I. Absorbance Spectra, Localization, and Discrimination from Other Yellow Pigments in Primate Retinas," Investigative Ophthalmology & Visual Science, Jun. 1984, pp. 660-673, vol. 25, No. 6.
Srivastava, A et al., "Nucleotide Sequence and Organization of the Adeno-Associated Virus 2 Genome," J. Virol., Feb. 1983, pp. 555-564, vol. 45, No. 2.
Strettoi, E. et al., "Modifications of retinal neurons in a mouse model of retinitis pigmentosa," PNAS, Sep. 26, 2000, pp. 11020-11025, vol. 97, No. 20.
Strettoi, E. et al., "Remodeling of second-order neurons in the retina of rd/rd mutant mice," Vision Res., 2003, pp. 867-877, vol. 43, No. 8.
Stringham, J. et al., "Enhancing Performance While Avoiding Damage: A Contribution of Macular Pigment," Invest. Ophthalmol. Vis. Sci., Sep. 2013, pp. 6298-6306, vol. 54, No. 9.
Surace, E. et al., "Versatility of AAV vectors for retinal gene transfer," Vision Res., Feb. 2008, pp. 353-359, vol. 48, No. 3.
Temple, S. et al., "Seasonal cycle in vitamin A1/A2-based visual pigment composition during the life history of coho salmon (Oncorhynchus kisutch)," J. Comp. Physiol. A., 2006, pp. 301-313, vol. 192, No. 3.
Tratschin, J-D. et al., "A Human Parvovirus, Adeno-Associated Virus, as a Eucaryotic Vector: Transient Expression and Encapsidation of the Procaryotic Gene for Chloramphenicol Acetyltransferase," Mol. Cell Biol., Oct. 1984, pp. 2072-2081, vol. 4, No. 10.
Tratschin, J-D. et al., "Adeno-Associated Virus Vector for High-Frequency Integration, Expression, and Rescue of Genes in Mammalian Cells," Mol. Cell. Biol., Nov. 1985, pp. 3251-3260, vol. 5, No. 11.
Tye, K. et al., "Amygdala circuitry mediating reversible and bidirectional control of anxiety," NIH Public Access Author Manuscript, available in PMC Aug. 10, 2011, pp. 1-11, Published in final edited form as: Nat., Mar. 17, 2011, pp. 358-362, vol. 471, No. 7338.
Vandenberghe, L. et al., "Novel adeno-associated viral vectors for retinal gene therapy," Gene Ther., 2012, pp. 162-168, vol. 19, Macmillan Publishers Limited.
Wald, G., "The Porphyropsin Visual System," J. Gen. Physiol., Jul. 20, 1939, pp. 775-794, vol. 22, No. 6.
Wenzel, A. et al., "Macular pigment optical density and photophobia light threshold," Vision Res., Dec. 2006, pp. 4615-4622, vol. 46, No. 28, Elsevier Ltd.
White, M. et al., "Massively parallel in vivo enhancer assay reveals that highly local features determine the cis-regulatory function of ChIP-seq peaks," PNAS, Jul. 16, 2013, pp. 11952-11957, vol. 110, No. 29.
Wong, A. et al., "Visual detection, pattern discrimination and visual activity in 14 strains of mice," Genes, Brain and Behavior, Jul. 2006, pp. 389-403, vol. 5, No. 5.
Yizhar, O. et al., "Neocortical excitation/inhibition balance in information processing and social dysfunction," NIH Public Access Author Manuscript, available in PMC Sep. 5, 2014, pp. 1-21, Published in final edited form as: Nature, Jul. 27, 2011, pp. 171-178, vol. 477, No. 7363.
Zhang, F. et al., "Red-shifted optogenetic excitation: a tool for fast neural control derived from Volvox carteri," NIH Public Access Author Manuscript, available in PMC Jun. 8, 2009, pp. 1-8, Published in final edited form as: Nat. Neurosci., Jun. 2008, pp. 631-633, vol. 11, No. 6.
Zhang, F. et al., "The Microbial Opsin Family of Optogenetic Tools," HHMI Author Manuscript, available in PMC Sep. 17, 2014, pp. 1-26, Published as: Cell., Dec. 23, 2011, pp. 1446-1457, vol. 147, No. 7, Elsvier Inc.
Akerboom, J. et al., "Genetically encoded calcium indicators for multi-color neural activity imaging and combination with optogenetics," Frontiers in Molecular Neuroscience, Mar. 2013, pp. 1-29, vol. 6, Article 2.
Alford, S. et al., "Optogenetic reporters," Biol. Cell, Jan. 2013, pp. 14-29, vol. 105, No. 1.
Allison, W. et al., "Visual pigment composition in zebrafish: Evidence for a rhodopsin-porphyropsin interchange system," Visual Neurosci., Nov.-Dec. 2004, pp. 945-952, vol. 21, No. 6, Cambridge University Press.
Arnson, H. et al., "Multielectrode Array Recordings of the Vomeronasal Epithelium," J. Visual Experiments, Mar. 2010, pp. 1-3, vol. 1, No. 37.
Bennett, J. et al., "Stable transgene expression in rod photoreceptors after recombinant adeno-associated virus-mediated gene transfer to monkey retina," PNAS, Aug. 1999, pp. 9920-9925, vol. 96, No. 17.
Bernstein, J. et al., "Optogenetics and thermogenetics: technologies for controlling the activity of targeted cells within intact neural circuits," NIH Public Access Author Manuscript, available in PMC Feb. 1, 2013, pp. 1-17, Published in final edited form as: Curr. Opin. Neurobiol., Feb. 2012, pp. 61-71, vol. 22, No. 1.
Bi, A. et al., "Ectopic Expression of a Microbial-Type Rhodopsin Restores Visual Responses in Mice with Photoreceptor Degeneration," NIH Public Access Author Manuscript, available in PMC Jul. 6, 2006, pp. 1-20, Published in final edited form as: Neuron., Apr. 6, 2006, pp. 23-33, vol. 50, No. 1.
Bone, R. et al., "Preliminary Identification of the Human Macular Pigment," Vision Res., 1985, pp. 1531-1535, vol. 25, No. 11, Pergamon Press Ltd., Great Britain.
Brustad, E et al., "Optimizing Non-natural Protein Function with Directed Evolution," NIH Public Access Author Manuscript, available in PMC Apr. 1, 2012, pp. 1-14, Published in final edited form as: Curr. Opin. Chem. Biol., Apr. 2011, pp. 201-210, vol. 15, No. 2.
Busskamp, V. et al., "Genetic Reactivation of Cone Photoreceptors Restores Visual Responses in Retinitis Pigmentosa," Science, Jul. 23, 2010, pp. 413-417, vol. 329.
Busskamp, V. et al., "Optogenetic therapy for retinitis pigmentosa," Gene Therapy, 2012, pp. 169-175, vol. 19, Macmillan Publishers Limited.
Byrne, L et al., "AAV-Mediated, Optogenetic Ablation of Muller Glia Leads to Structural and Functional Changes in the Mouse Retina," PLos ONE, Sep. 2013, pp. 1-13, vol. 8, Issue 9, e76075.
Caporale, N. et al., "LiGluR Restores Visual Responses in Rodent Models of Inherited Blindness," Mol. Ther., Jul. 2011, pp. 1212-1219, vol. 19, No. 7.
Chinen, A. et al., "Reconstitution of Ancestral Green Visual Pigments of Zebrafish and Molecular Mechanism of Their Spectral Differentiation," Mol. Biol. Evolution, Apr. 2005, pp. 1001-1010, vol. 22, No. 4.
Coon, M., "Cytochrome P450: Natures Most Versatile Biological Catalyst," Annu. Rev. Pharmacol. Toxicol., 2005, pp. 1-25, vol. 45.

(56) References Cited

OTHER PUBLICATIONS

Corbo, J. et al., "Characterization of a notochord-specific enhancer from the Brachyury promoter region of the ascidian, Ciona intestinalis," Development, 1997, pp. 589-602, vol. 124, No. 3, The Company of Biologists Limited, Great Britain.

Corbo, J. et al., "The Ascidian as a Model Organism in Development and Evolutionary Biology," Cell, Sep. 7, 2001, pp. 535-538, vol. 106, No. 5, Cell Press.

Corbo, J. et al., "CRX ChIP-seq reveals the cis-regulatory architecture of mouse photoreceptors," Genome Res., Nov. 2010, pp. 1512-1525, vol. 20, No. 11, Cold Spring Harbor Laboratory Press.

Crick, F., "The impact of molecular biology on neuroscience," Phil. Trans. R. Soc. Lond. B, Dec. 29, 1999, pp. 2021-2025, vol. 354, No. 1392, The Royal Society.

Dahlem, T. et al., "Simple Methods for Generating and Detecting Locus-Specific Mutations Induced with TALENs in the Zebrafish Genome," PLoS ONE, Aug. 2012, pp. 1-15, vol. 8, Issue 8, e1002861.

Dalkara, D. et al., "AAV Mediated GDNF Secretion From Retinal Glia Slows Down Retinal Degeneration in a Rat Model of Retinitis Pigmentosa," Mol. Ther., Sep. 2011, pp. 1602-1608, vol. 19, No. 9.

Dalkara, D. et al., "In Vivo-Directed Evolution of a New Adeno-Associated Virus for Therapeutic Outer Retinal Gene Delivery from the Vitreous," Sci. Transl. Med., Jun. 12, 2013, pp. 1-11, vol. 5, Issue 189, 189ra76.

Degenaar, P. et al., "Optobionic vision—a new genetically enhanced light on retinal prosthesis," J. Neural. Eng., 2009, pp. 1-10, vol. 6, IOP Publishing Ltd., United Kingdom.

Dhingra, A. et al., "Probing Neurochemical Structure and Function of Retinal on Bipolar Cells with a Transgenic Mouse," NIH Public Access Author Manuscript, available in PMC Apr. 14, 2010, pp. 1-26, Published in final edited form as: J. Comp. Neural., Oct. 10, 2008, pp. 484-496, vol. 510, No. 5.

Doroudchi, M. et al., "Towards Optogenetic Sensory Replacement," NIH Public Access Author Manuscript, available in PMC Apr. 26, 2013, pp. 1-6, Published in final edited form as: Conf. Proc. IEEE Eng. Med. Biol. Soc., 2011, pp. 3139-3141, vol. 2011.

Doroudchi, M. et al., "Virally delivered Channelrhodopsin-2 Safely and Effectively Restores Visual Function in Multiple Mouse Models of Blindness," Mol Ther., Jul. 2011, pp. 1220-1229, vol. 19, No. 7.

Duque, S. et al., "Intravenous Administration of Self-complementary AAV9 Enables Transgene Delivery to Adult Motor Neurons," Mol Ther., Jul. 2009, pp. 1187-1196, vol. 17, No. 7.

Fossat, N. et al., "A new GFP-tagged line reveals unexpected Otx2 protein localization in retinal photoreceptors," BMD Developmental Biol., Nov. 2, 2007, pp. 1-11, vol. 7, No. 122, BioMedCentral.

Gao, G. et al., "Clades of Adeno-Associated Viruses Are Widely Disseminated in Human Tissues," J. Virol., Jun. 2004, pp. 6381-6388, vol. 78, No. 12, American Society for Microbiology.

Govorunova, E. et al., "New Channelrhodopsin with a Red-Shifted Spectrum and Rapid Kinetics from Mesostigma wide," May-Jun. 2011, pp. 1-9, vol. 2, Issue 3, e00115-11.

Grieger, J. et al., "Packaging Capacity of Adeno-Associated Virus Serotypes: Impact of Larger Genomes on Infectivity and Postentry Steps," J. Virol., Aug. 2005, pp. 9933-9944, vol. 79, No. 15, American Society for Microbiology.

Harosi, F., "An Analysis of Two Spectral Properties of Vertebrate Visual Pigments," Vision Res., 1994, pp. 1359-1367, vol. 34, No. 11, Elsevier Science Ltd., Great Britain.

Hayashi, S. et al., "Efficient Recombination in Diverse Tissues by a Tamoxifen-Inducible Form of Cre: A Tool for Temporally Regulated Gene Activation/Inactivation in the Mouse," Developmental Biol., 2002, pp. 305-318, vol. 244, Elsevier Science, USA.

Hermonat, P. et al., "Use of adeno-associated virus as a mammalian DNA cloning vector: Transduction of neomycin resistance into mammalian tissue culture cells," PNAS, Oct. 1984, pp. 6366-6470, vol. 81.

International Search Report and Written Opinion dated May 20, 2015 from related International Patent Application Serial No. PCTUS2015021153; 10 pgs.

Jacobs, G. et al., "Emergence of Novel Color Vision in Mice Engineered to Express a Human Cone Photopigment," Science, Mar. 23, 2007, pp. 1723-1725, vol. 315, No. 5819.

Jacobson, S. et al., "Gene Therapy for Leber Congenital Amaurosis caused by RPE65 mutations: Safety and Efficacy in Fifteen Children and Adults Followed up to Three Years," NIH Public Access Author Manuscript, available in PMC Mar. 18, 2003, pp. 1-27, Published in final edited form as: Arch. Ophthalmol., Jan. 2012, pp. 9-24, vol. 130, No. 1.

Kavanagh, K. et al., "The SDR superfamily: functional and structural diversity within a family of metabolic and regulatory enzymes," Cell. Mol. Life Sci., 2008, pp. 3895-3906, vol. 65, Birkhauser Verlag, Basel.

Kim, D. et al., A Core Paired-Type and POU Homeodomain-Containing Transcription Factor Program Drives Retinal Bipolar Cell Gene Expression, NIH Public Access Author Manuscript, available in PMC Jul. 23, 2009, pp. 1-38, Published in final edited form as: J. Neurosci., Jul. 30, 2008, pp. 7748-7764, vol. 28, No. 31.

Klimczak, R. et al., "A Novel Adeno-Associated Viral Variant for Efficient and Selective Intravitreal Transduction of Rat Muller Cells," PLoS ONE, Oct. 2009, pp. 1-10, vol. 4, No. 10, e7467.

Koerber, J. et al., "Construction of diverse adeno-associated viral libraries for directed evolution of enhanced gene delivery vehicles," Nat. Protocols, 2006, pp. 701-706, vol. 1, No. 2.

Koerber, J. et al., "DNA Shuffling of Adeno-associated Virus Yields Functionally Diverse Viral Progeny," NIH Public Access Author Manuscript, available in PMC May 18, 2009, pp. 1-17, Published in final edited form as: Mol. Ther., Oct. 2008, pp. 1703-1709, vol. 16, No. 10.

Kwasnieski, J. et al., "Complex effects of nucleotide variants in a mammalian cis-regulatory element," PNAS, Nov. 20, 2012, pp. 19498-19503, vol. 109, No. 47.

Lagali, P. et al., "Light-activated channels targeted to ON bipolar cells restore visual function in retinal degeneration," Nat. Neurosci., Jun. 2008, pp. 667-675, vol. 11, No. 6.

Langevin, L. et al., "Validating in Utero Electroporation for the Rapid Analysis of Gene Regulatory Elements in the Murine Telencephalon," Developmental Dynamics, 2007, pp. 1273-1286, vol. 236, Wiley-Liss, Inc.

Lee, J. et al., "Quantitative fine-tuning of photoreceptor cis-regulatory elements through affinity modulation of transcription factor binding sites," Gene Ther., 2010, pp. 1390-1399, vol. 17, Macmillan Publishers Limited.

Leproust, E. et al., "Synthesis of high-quality libraries of long (150mer) oligonucleotides by a novel depurination controlled process," Nuc. Acids Res., 2010, pp. 2522-2540, vol. 38, No. 8.

Lin, B. et al "Restoration of visual function in retinal degeneration mice by ectopic expression of melanopsin," PNAS, Oct. 14, 2008, pp. 16009-16014, vol. 105, No. 41.

Lin, J. et al., "ReaChR: A red-shifted variant of channelrhodopsin enables deep transcranial optogenetic excitation," HHS Public Access Author Manuscript, available in PMC Apr. 1, 2014, pp. 1-29, Published in final edited form as: Nat. Neurosci., Oct. 2013, pp. 1499-1508, vol. 16, No. 10.

Maheshri, N. et al., "Directed evolution of adeno-associated virus yields enhanced gene delivery vectors," Nat. Biotechnol., Feb. 2006, pp. 198-204, vol. 24, No. 2.

\* cited by examiner

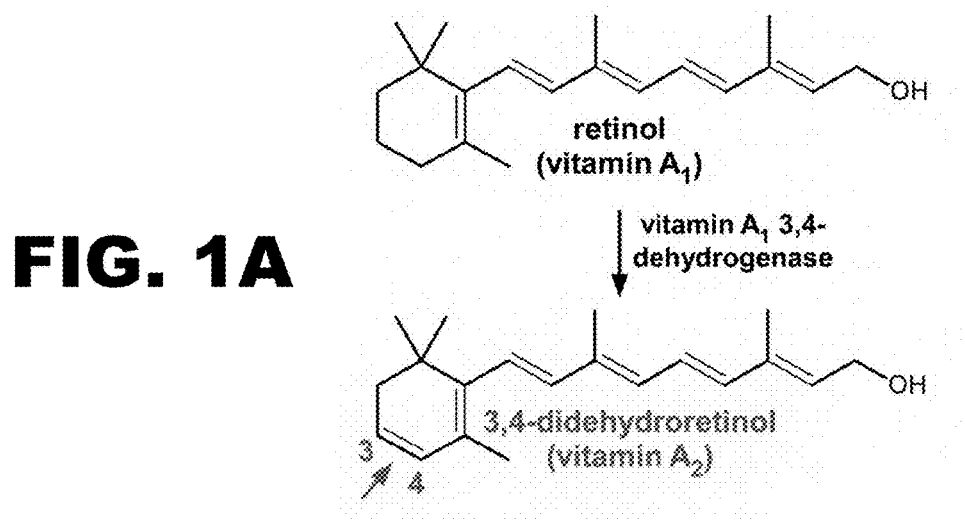
FIG. 1A
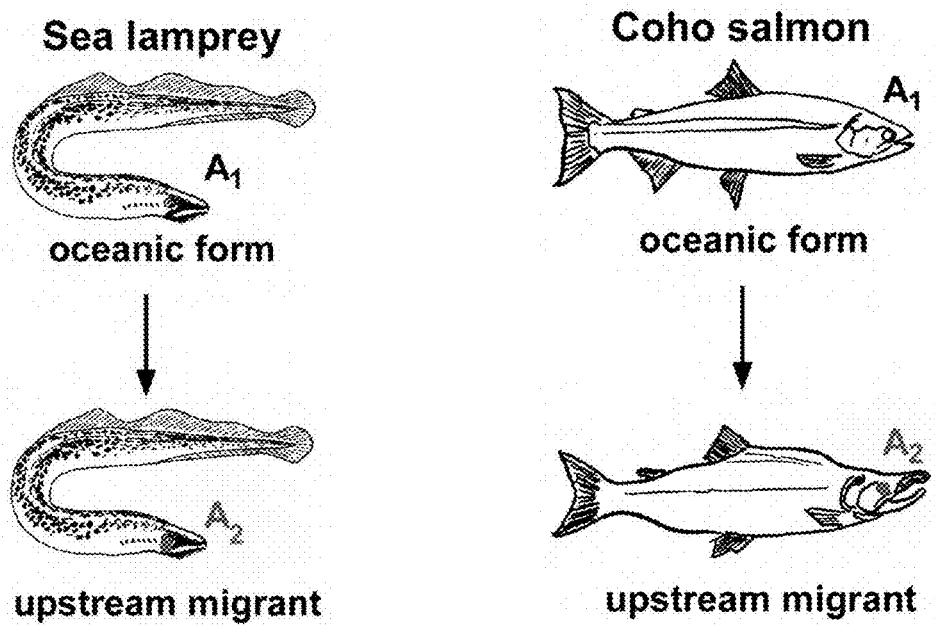
FIG. 1B  FIG. 1C

TH, +/+

TH, A1, +/+

TH, A4, +/+

TH, A1/A4

CON, +/+

CON, A1, +/+

CON, A4, +/+

CON, A1/A4

Cyp27c1

FIG. 9

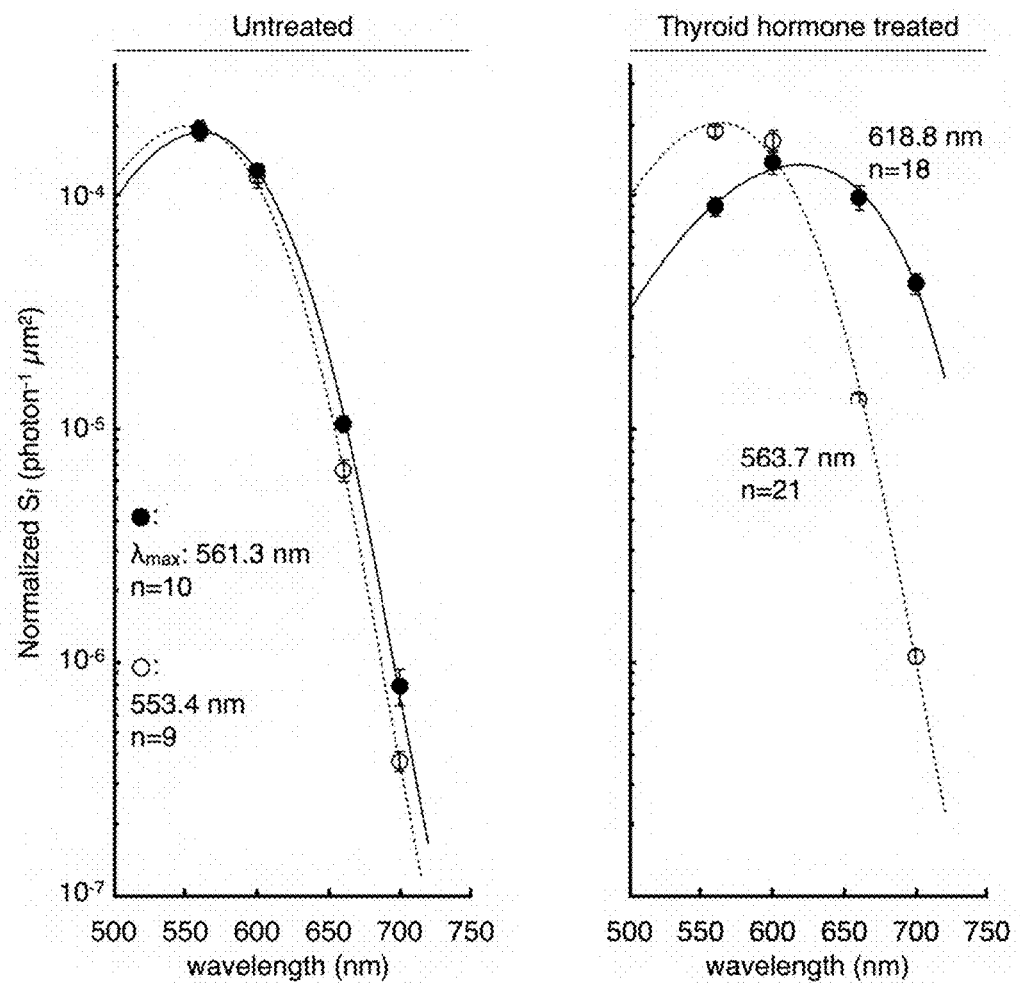
FIG. 11A   FIG. 11B

METHODS AND COMPOSITIONS FOR RED-SHIFTED CHROMOPHORE SUBSTITUTION FOR OPTOGENETIC APPLICATIONS

CROSS REFERENCE TO RELATED APPLICATIONS

This application claims the benefit of PCT Application PCT/US2015/021153, filed Mar. 18, 2015, which claims the benefit of U.S. provisional application No. 61/955,074, filed Mar. 18, 2014 and U.S. provisional application No. 62/014,289, filed Jun. 19, 2014, each of the disclosures of which is hereby incorporated by reference in its entirety.

GOVERNMENTAL RIGHTS

This invention was made with government support under EY018826 awarded by National Institutes of Health (NIH). The government has certain rights in the invention.

FIELD OF THE INVENTION

The present disclosure provides compositions and methods used for optogenetics, wherein the composition comprises an optogenetic device and a retinoid processing enzyme. The present disclosure encompasses a novel biomimetic strategy for red-shifting optogenetic devices.

BACKGROUND OF THE INVENTION

Optogenetics is one of the most important technological breakthroughs in neuroscience during the past decade, and holds tremendous promise for dissecting the mechanisms of neurologic disease and for treating a range of disorders. Optogenetic devices are ion channels or pumps that can be regulated by light, thus permitting the investigator to turn neuronal activity on and off with high spatial and temporal precision. Optogenetic devices come in two basic varieties: optogenetic activators which cause a cell to depolarize upon exposure to light and optogenetic inhibitors which cause a cell to hyperpolarize. Since optogenetic devices are genetically encoded, their expression can be precisely targeted to defined subpopulations of cells for both experimental and therapeutic purposes.

Optogenetic approaches can be applied to virtually any organ system, but they are particularly useful in electrically active cells. For this reason, most research using optogenetic approaches has focused on the brain, the retina, and the heart. In basic studies, optogenetic tools permit a scientist to exert unprecedented control over the activity of neuronal circuits, thus allowing a deeper understanding of circuit function. In the applied arena, a range of therapeutic applications of optogenetics can be envisioned. First, in combination with recently developed wireless LED devices, optogenetic approaches may soon permit the direct stimulation of subpopulations of brain cells within defined nuclei without the need for invasive, indwelling electrodes. This kind of therapy could eventually revolutionize treatment of diseases such as Parkinson's disease, which in some cases is treated with chronic electrodes placed in the subthalamic nuclei.

Another potential application would be as an 'all optical' pacemaker in the heart of patients with cardiac arrhythmias. Currently, such patients require cumbersome indwelling wires to be implanted in the tissues of their heart. With optogenetics, one could target the pacemaker cells themselves with optogenetic devices (via a gene therapy vector such as adeno-associated virus [AAV]) and then implant a minute wireless LED device to control the cells. This approach could greatly simplify the use of pacemakers and improve the lives of the many patients requiring them.

There are over 200 genetically distinct forms of retinal degeneration that cause severe vision loss or complete blindness in millions of people worldwide. Both simple (Mendelian) and complex (non-Mendelian) forms of retinal degeneration exist. The final common pathogenetic mechanism in all of these conditions is the progressive loss of both rod and cone photoreceptors via cell death. Once photoreceptors are lost, blindness ensues. There is no cure for any of these genetic forms of blindness.

In contrast to traditional gene therapy that attempts to replace or repair a defective gene or bypass the genetic defect through correction of the protein deficiency or dysfunction, optogenetic approaches to therapy can be used to endow normally non-photosensitive cells in the retina with the ability to respond to light, thus restoring useful vision to the patient. Unlike retinal chip implants that provide extracellular electrical stimulation to bipolar or ganglion cells, optogenetics-based therapies stimulate the cells from inside the cell.

The most commonly used optogenetic devices operate in the 450-600 nm range, presenting two challenges to the investigator: (1) light in this range is strongly scattered and absorbed by neural tissue and blood, limiting the tissue depth at which optogenetic devices can be effectively utilized; and (2) many optogenetic sensors that report physiological states (e.g., calcium levels or voltage) have activation or emission spectra that strongly overlap the wavelength range of the optogenetic devices, thus complicating their simultaneous use. Thus there is a need for optogenetic devices with red-shifted excitation spectra, because longer wavelength light penetrates more deeply into tissue and red-shifting reduces the spectral overlap with sensors.

SUMMARY OF THE INVENTION

In an aspect, the present disclosure encompasses a polynucleotide sequence encoding a polypeptide, the polypeptide comprising at least one optogenetic device and a retinoid processing enzyme.

In another aspect, the present disclosure encompasses a composition comprising a vector. The vector comprises a polynucleotide sequence encoding a polypeptide, the polypeptide comprising at least one optogenetic device and a retinoid processing enzyme.

In still another aspect, the present disclosure encompasses a composition comprising two vectors. A first vector comprises a polynucleotide sequence encoding a polypeptide, the polypeptide comprising at least one optogenetic device. A second vector comprises a polynucleotide sequence encoding a polypeptide, the polypeptide comprising a retinoid processing enzyme.

In still yet another aspect, the present disclosure encompasses a method of restoring sensitivity to light in an inner retinal cell. The method comprises administering to the cell a composition comprising a vector. The vector comprises a polynucleotide sequence encoding a polypeptide, the polypeptide comprising at least one optogenetic device and a retinoid processing enzyme.

In a different aspect, the present disclosure encompasses a method of restoring vision to a subject. The method comprises identifying a subject with loss of vision due to a deficit in light perception or sensitivity; administering a composition comprising a vector, the vector comprising a polynucleotide sequence encoding a polypeptide, the polypeptide comprising at least one optogenetic device and a retinoid processing enzyme; activating the optogenetic device with light; and measuring light sensitivity in the subject, wherein increased light sensitivity indicates vision restoration.

In other aspects, the present disclosure encompasses a method of treating retinal degeneration in a subject. The method comprises identifying a subject with retinal degeneration due to loss of photoreceptor function; administering a composition comprising a vector, the vector comprising a polynucleotide sequence encoding a polypeptide, the polypeptide comprising at least one optogenetic device and a retinoid processing enzyme; and measuring light-sensitivity in the subject, wherein increased sensitivity to light indicates treatment of retinal degeneration.

In certain aspects, the present disclosure encompasses a method of restoring photoreceptor function in a human eye. The method comprises administering an effective amount of composition comprising a vector, the vector comprising a polynucleotide sequence encoding a polypeptide, the polypeptide comprising at least one optogenetic device and a retinoid processing enzyme.

In certain different aspects, the present disclosure encompasses a method of extending tissue depth at which an optogenetic device can function. The method comprises administering a composition comprising a vector, the vector comprising a polynucleotide sequence encoding a polypeptide, the polypeptide comprising at least one optogenetic device and a retinoid processing enzyme.

In still other aspects, the present disclosure encompasses a method of red-shifting the activation wavelength of an optogenetic device in a subject. The method comprises administering a composition comprising a vector, the vector comprising a polynucleotide sequence encoding a polypeptide, the polypeptide comprising at least one optogenetic device and a retinoid processing enzyme.

In yet other aspects, the present disclosure encompasses a method of depolarizing an electrically active cell. The method comprises administering to the cell a composition comprising a vector, the vector comprising a polynucleotide sequence encoding a polypeptide, the polypeptide comprising at least one optogenetic device and a retinoid processing enzyme, wherein the optogenetic device comprises an optogenetic activator.

In still yet other aspects, the present disclosure encompasses a method of hyperpolarizing an electrically active cell. The method comprises administering to the cell a composition comprising a vector, the vector comprising a polynucleotide sequence encoding a polypeptide, the polypeptide comprising at least one optogenetic device and a retinoid processing enzyme, wherein the optogenetic device comprises an optogenetic inhibitor.

BRIEF DESCRIPTION OF THE FIGURES

The application file contains at least one photograph executed in color. Copies of this patent application publication with color photographs will be provided by the Office upon request and payment of the necessary fee.

FIG. 1A, FIG. 1B, FIG. 1C, FIG. 1D, FIG. 1E, FIG. 1F, FIG. 1G, FIG. 1H, FIG. 1I, FIG. 1J and FIG. 1K depict images and graphs showing that diverse species employ a vitamin $A_1$ to vitamin $A_2$ switch to red-shift the spectral sensitivity of their photoreceptors. (FIG. 1A) Depicts the conversion of all-trans retinol (vitamin $A_1$) into all-trans 3,4-didehydroretinol (vitamin $A_2$). (FIG. 1B, FIG. 1C, FIG. 1D) Depict several species that switch between the use of vitamin $A_1$ and vitamin $A_2$ for vision at different stages of their life cycle. (FIG. 1B) Sea lamprey; (FIG. 1C) Coho salmon; and (FIG. 1D) Northern leopard frog. (FIG. 1E, FIG. 1F, FIG. 1G, FIG. 1H) depict graphs showing that thyroid hormone treatment of adult zebrafish induces quantitative conversion of retinol into 3,4-didehydroretinol. Adult zebrafish were treated with 300 µg/liter thyroid hormone (L-thyroxine) in their water for three weeks. The retinas were then harvested, and retinoid extracts were reduced with sodium borohydride and analyzed by HPLC. (FIG. 1E) Depicts the position of peak #1 in control zebrafish. (FIG. 1F) Depicts the position of peak #2 in TH-treated zebrafish. (FIG. 1G) The predominant species form untreated control retinas was retinol (solid black curve) with a peak at 326 nm. (FIG. 1H) The predominant species in thyroid hormone-treated retinas was 3,4-dedihydroretinol (solid black curve) with a red-shifted peak at 355 nm. Spectra of commercially produced retinol and 3,4-didehydroretinol standards are shown in (FIG. 1G) and (FIG. 1H), respectively, as dotted red curves. (FIG. 1I, FIG. 1J, FIG. 1K) depict the HPLC profile of retinoids in the dorsal (FIG. 1J) and ventral (FIG. 1K) bullfrog (*Lithobates catesbeianus*) retinal pigment epithelium (RPE). Note that only vitamin $A_1$ and its derivatives (the retinal form has been reduced to the alcohol form) are detected in the ventral RPE whereas both vitamin $A_1$ and vitamin $A_2$ are present in nearly equal proportions in the dorsal RPE.

(FIG. 2A) RNA-seq results comparing the expression levels of individual transcripts (shown as black circles) from RPE derived from zebrafish treated for 3 weeks with thyroid hormone and vehicle-treated controls. The location of the Cyp27c1 transcript is circled in red. (FIG. 2B) RNA-seq results comparing the expression levels of individual transcripts (shown as black circles) from dorsal and ventral bullfrog RPE. The location of the Cyp27c1 transcript is circled in red. In both cases, Cyp27c1 stands out as being markedly upregulated.

(FIG. 4A) Cyp27c1 is expressed on the dorsal side but not the ventral side in the bullfrog eye. (FIG. 4B) Cyp27c1 is expressed in thyroid hormone treated zebrafish.

(FIG. 5A, FIG. 5B, FIG. 5C) shows the HPLC profiles of retinoids extracted from cells transfected with (FIG. 5A) an empty control vector (negative control) and from cells transfected with (FIG. 5B) an expression vector containing zebrafish Cyp27c1 or (FIG. 5C) an expression vector containing human Cyp27c1 and incubated overnight with retinol. Note the formation of significant quantities of 3,4-didehydroretinol ($A_2$) in the Cyp27c1 transfected cells. (FIG. 5D, FIG. 5E) depicts the HPLC profile of commercially obtained chemical standards $A_1$ (FIG. 5D) and $A_2$ (FIG. 5E).

FIG. 9 depicts a Western blot showing that Cyp27c1 protein cannot be identified in the RPE of thyroid hormone-treated Cyp27c1 null mutant fish.

(FIG. 10A) Depicts the HPLC profile of thyroid hormone treated wild-type zebrafish showing conversion of $A_1$ to $A_2$. (FIG. 10B) Depicts the HPLC profile of untreated wild-type zebrafish showing only the presence of $A_1$. (FIG. 10C) Depicts the HPLC profile of thyroid hormone treated cyp27c1 null mutant zebrafish showing only the presence of $A_1$. (FIG. 10D) Depicts the HPLC profile of untreated cyp27c1 null mutant zebrafish showing only the presence of $A_1$.

FIG. 11A and FIG. 11B depict graphs presenting suction electrode recordings of red single cones from wild-type and Cyp27c1 mutant fish. The mutant fish fail to red-shift the sensitivity of their red cones after thyroid hormone treatment. (FIG. 11A) Untreated wild-type and mutant zebrafish have similar sensitivity. (FIG. 11B) Thyroid hormone treated cyp27c1 mutant zebrafish fail to red-shift their photoreceptor sensitivity.

DETAILED DESCRIPTION OF THE INVENTION

Figure 1D:
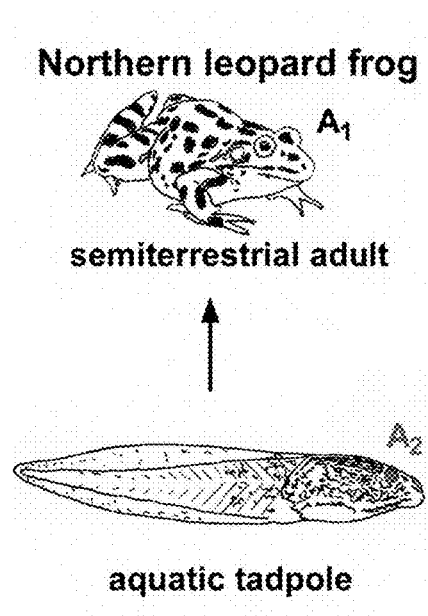

The present invention encompasses compositions and methods used for optogenetics. The present invention encompasses a novel biomimetic strategy for red-shifting optogenetic devices: red-shifted chromophore substitution. A key feature of the approach is that chromophore substitution can be coupled to the use of an existing optogenetic device thereby shifting the sensitivity of the device toward the red end of the light spectrum, regardless of its original wavelength sensitivity. This has the added benefit of permitting the use of optogenetic devices at greater tissue depths. For example, expression of the retinoid processing enzyme, Cyp27c1, can be used to extend the tissue depth at which co-expressed optogenetic devices can operate because it will permit the optogenetic device to be responsive to longer wavelength light which can penetrate tissue more readily. This approach could have important implications for optogenetics-based therapies in the large human brain and in human cardiac tissue which is highly opaque to shorter wavelength light. In addition, co-expression of Cyp27c1 can be applied to optogenetic strategies for treating blindness.

I. Optogenetic Device

In an aspect, the present invention provides an optogenetic device. An "optogenetic device" which may be used interchangeably with "optogenetic actuator" refers to a photochemically reactive polypeptide that uses Vitamin A or isoforms thereof as its chromophore. Vitamin A isoforms have a beta-ionone ring to which an isoprenoid chain is attached, called a retinyl group. There are three prototypical forms of Vitamin A: Vitamin $A_1$, Vitamin $A_2$ and Vitamin $A_3$. Vitamin $A_1$ isoforms may include retinol, retinal and retinoic acid. Vitamin $A_2$ isoforms may include 3,4-didehydroretinol, 3,4-didehydroretinal and 3,4-didehydroretinoic acid. Vitamin $A_3$ isoforms may include 3-hydroxyretinol, 3-hydroxyretinal and 3-hydroxyretinoic acid. Additionally, Vitamin A may be found in various configurations such as all-trans, 11-cis, and 13-cis. An optogenetic device is a light-gated ion pump or channel that absorbs light and is activated by light. An optogenetic device of the invention may be from a prokaryotic organism or a eukaryotic organism. An optogenetic device of the invention may be a microbial opsin or a vertebrate opsin. A common feature of an optogenetic device is that it contains seven membrane-embedded α-helices that form an internal pocket in which the retinal is bound serving as an antenna for photons. A general property of an optogenetic device is the attachment of retinal to the ε-amino group of a lysine in the seventh helix of the structure. Upon absorption of a photon, retinal isomerizes and triggers a sequence of conformational changes within the opotogenetic device. Generally, retinal isomerizes from the all-trans configuration to the 13-cis configuration (in microbial opsins) or from the 11-cis configuration to the all-trans configuration (in vertebrate-type opsins) upon absorption of a photon. An optogenetic device of the invention may use all-trans retinal and/or 11-cis retinal as its chromophore. In a specific embodiment, an optogenetic device of the invention utilizes all-trans retinal as its chromophore. When an optogenetic device absorbs a photon, its all-trans retinal chromophore isomerizes to the 13-cis configuration. An optogenetic device may be an optogenetic activator or an optogenetic inhibitor.

An optogenetic activator causes a cell to depolarize upon exposure to light. When a cell depolarizes, the negative internal charge of the cell becomes positive for a brief period. The shift from a negative to a positive internal cellular environment allows the transmission of electrical impulses both within a cell and, optionally, between cells. An optogenetic actuator may be a microbial opsin or a vertebrate opsin. Non-limiting examples of vertebrate opsins include visual opsins (e.g. rhodopsins, photopsins), melanopsins, pinopsins, parapinopsins, VA opsins, peropsins, neuropsins, encephalopsins, retinochromes, and RGR opsins. In a specific embodiment, an optogenetic activator of the invention is a light-gated ion channel that upon absorption of a photon transports cations. Any suitable light-gated, retinal-dependent, ion channel that transports cations upon absorption of a photon may be used as an optogenetic activator of the invention. Non-limiting examples of optogenetic activators may include channelrhodopsin-1, channelrhodopsin-2, or variants thereof. Numerous variants of channelrhodopsin are being generated to improve certain features of these proteins. Based on the mechanism of action of the invention, it is contemplated to these variants of channelrhodopsin and other similar microbial opsins with both an opsin domain and a channel domain will function in the invention. In a specific embodiment, an optogenetic activator of the invention is a red-shifted optogenetic activator. Non-limiting examples of red-shifted optogenetic activators may include a red-shifted channelrhodopsin-1 (ChR1), such as Volvox ChR1 (VChR1) (Zhang et al., 2008), *M. viride* ChR1 (MChR1) (Govorunova et al., 2011), or C1V1s, a family of ChR1/VChR1 chimeras (Yizhar et al., 2011), and a red-shifted ChR2. In an exemplary embodiment, a red-shifted optogenetic activator of the invention is red-activatable channelrhodopsin (ReaChR).

An optogenetic inhibitor causes a cell to hyperpolarize upon exposure to light. When a cell hyperpolarizes, the negative internal charge of the cell becomes more negative for a brief period. The shift to more negative inhibits action potentials by increasing the stimulus required to move the membrane potential to the action potential threshold. In a specific embodiment, an optogenetic inhibitor is a light-gated ion pump that upon absorption of a photon transports chloride ions inward and/or transports cations outward. Any suitable light-gated, retinal-dependent, ion pump that transports chloride ions inward or cations outward upon absorption of a photon may be used as an optogenetic inhibitor of the invention. Non-limiting examples of optogenetic inhibitors include halorhodopsins, bacteriorhodopsins, proteorhodopsins, and xanthorhodopsins. Numerous variants of light-gated ion pumps are being generated to improve certain features of these proteins. Based on the mechanism of action of the invention, it is contemplated to these variants of light-gated ion pumps will function in the invention. Non-limiting specific examples of optogenetic inhibitors include halorhodopsin (NpHR) (Accession number: J05199.1), enhanced halorhodopsins (eNpHR2.0 and eNpHR3.0), archaerhodopsin-3 (AR-3), archaerhodopsin (Arch) (Accession Number: J05165.1), *Leptosphaeria maculans* fungal opsins (Mac) (Accession Number: AF290180.1), enhanced bacteriorhodopsin (eBR), and new light-driven pumps such as Halo57, a naturally occurring halorhodopsin (HR) (Klapoetke et al., 2010), and variants thereof. In an exemplary embodiment, an optogenetic inhibitor of the invention is eNpHR3.0.

II. Retinoid Processing Enzyme

Figure 1E:
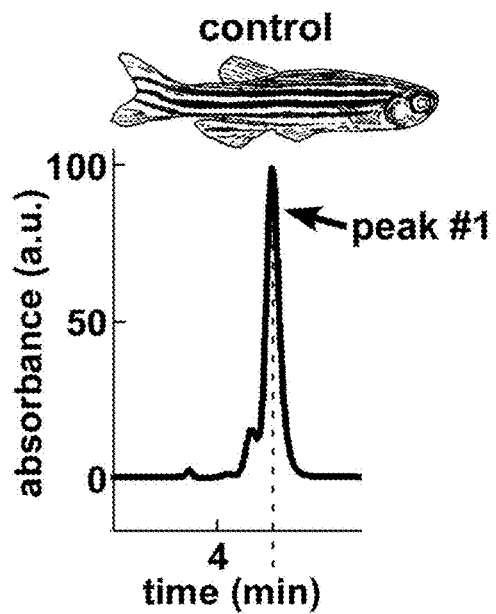
Figure 1F:
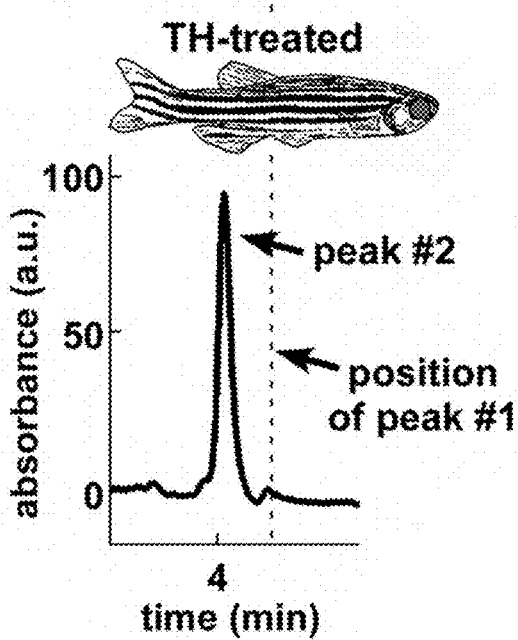
Figure 1G:
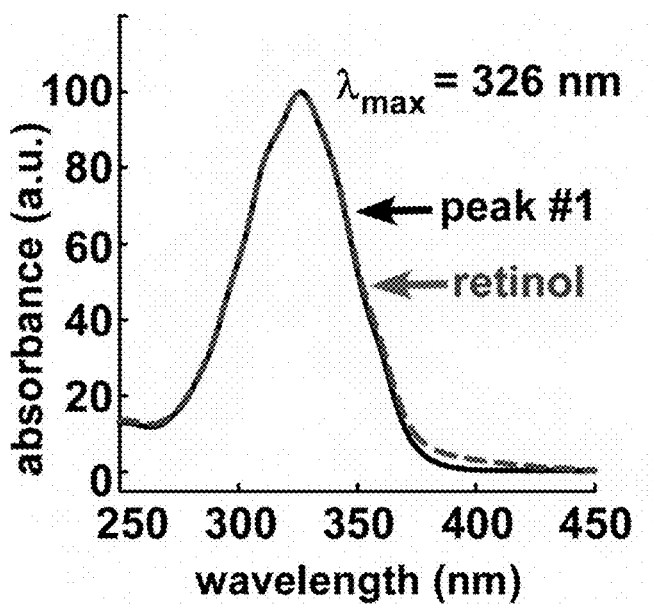
Figure 1H:
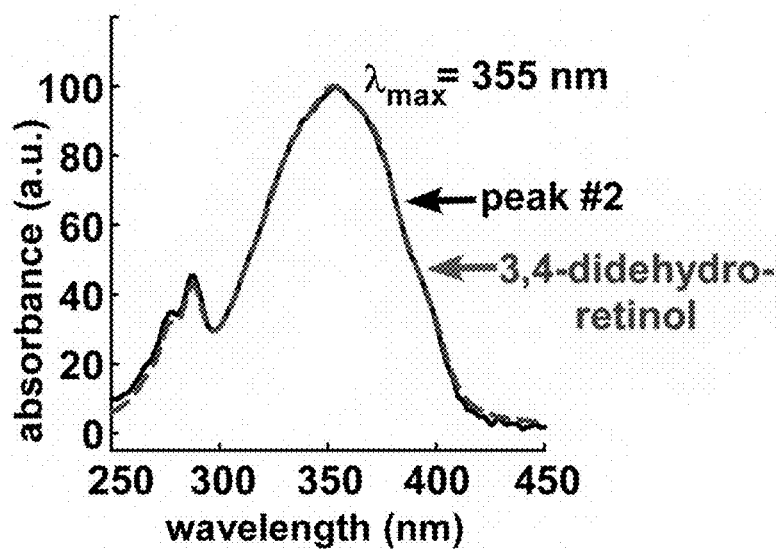

In an aspect, the present invention provides a retinoid processing enzyme. A retinoid processing enzyme of the invention is a polypeptide that converts Vitamin $A_1$ into Vitamin $A_2$. For example, a retinoid processing enzyme of the invention is a polypeptide that converts retinol into 3,4-didehydroretinol, or retinal into 3,4-didehydroretinal, or retinoic acid into 3,4-didehydroretinoic acid. Vitamin $A_2$ differs from Vitamin $A_1$ in having an additional double bound between carbon 3 and carbon 4 of the β-ionone ring (see FIG. 1A). The conversion of Vitamin $A_1$ into Vitamin $A_2$, red-shifts the sensitivity of an optogenetic device of the invention. For example, FIG. 1E,F shows that Vitamin $A_1$ has an absorbance maximum of 326 nm, whereas Vitamin $A_2$ has an absorbance maximum of 355 nm. The presence of an additional double bond in the β-ionone ring of Vitamin $A_2$ results in an optogenetic device that absorbs light at longer wavelengths as compared to those with Vitamin $A_1$. By red-shift is meant that the light that an optogenetic device is sensitive to is increased in wavelength, or shifted to the red end of the spectrum. An increase in wavelength is equivalent to a lower frequency and a lower photon energy.

In an embodiment, a retinoid processing enzyme may be a retinol dehydrogenase (RDH) in the EC 1.1.1.105 enzyme class. An enzyme in this class recognizes all-trans-retinol and all-trans-retinal as substrates and exhibits a strong preference for NAD(+)/NADH as cofactors. The systematic name of this enzyme class is retinol:NAD+ oxidoreductase. Other names in common use include retinol (Vitamin $A_1$) dehydrogenase, MDR, microsomal retinol dehydrogenase, all-trans-retinol dehydrogenase, retinal reductase, and retinene reductase. In a preferred embodiment, a retinoid processing enzyme may be a retinol 3,4-dehydrogenase. In an exemplary embodiment, the retinoid processing enzyme is cytochrome P450, family 27, subfamily C, polypeptide 1 (Cyp27c1). This gene encodes a member of the cytochrome P450 superfamily of enzymes. The cytochrome P450 proteins are monooxygenases which catalyze many reactions involved in drug and xenobiotic metabolism and synthesis of cholesterol, steroids, retinoids and other lipids. For example, a retinoid processing enzyme may be encoded by the cyp27c1 gene from *Homo sapiens* or a homolog thereof (GenBank accession number NM_001001665.3). In another example, a retinoid processing enzyme may be encoded by the cyp27c1 gene from *Danio rerio* or a homolog thereof (GenBank accession number NM_001113337.2). A retinoid processing enzyme may also be an analogue, active fragment or derivative of Cyp27c1, having an activity as described in the present invention.

A skilled artisan will appreciate that homologs of Cyp27c1 can be found in a variety of species. Non-limiting examples include dog (XM_005631886.1, XM_005631885.1, XM_005631884.1), cattle (XM_010801827.1, XM_010801825.1, XM_002685217.4), chicken (XM_004942891.1, XM_422077.3), catfish (JT408218.1), and marine medaka (JX454644). It is appreciated that the present invention is directed to homologs of Cyp27c1 in other organisms and is not limited to the zebrafish and human homolog. Homologs can be found in other species by methods known in the art. In determining whether a retinoid processing enzyme has significant homology or shares a certain percentage of sequence identity with a sequence of the invention, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details.

A retinoid processing enzyme of the invention may be at least 65, 70, 75, 80, 85, 90, or 95% homologous to Cyp27c1 provided it has the same activity as the zebrafish and/or human Cyp27c1. In certain embodiments, a retinoid processing enzyme of the invention may be at least 65, 66, 67, 68, 69, or 70% homologous to Cyp26c1 provided it has the same activity as the zebrafish and/or human Cyp27c1. In different embodiments, a retinoid processing enzyme of the invention may be at least 71, 72, 73, 74, 75, 76, 77, 78 or 79% homologous to Cyp26c1 provided it has the same activity as the zebrafish and/or human Cyp27c1. In one embodiment, a retinoid processing enzyme of the invention may be at least 80, 81, 82, 83, 84, 85, 86, 87, 88, or 89% homologous to Cyp27c1. In another embodiment, a retinoid processing enzyme of the invention may be at least 90, 91, 92, 93, 94, 95, 96, 97, 98, 99, or 100% homologous to Cyp27c1. In yet another embodiment, a retinoid processing enzyme may be a truncation or variant that has the same activity as the full length Cyp27c1. Further, if the Cyp27c1 is not human, the Cyp27c1 may be codon optimized for optimal expression in human. Methods of codon optimizing a nucleic acid are known in the art.

III. Optogenetic Constructs

The invention provides various optogenetic constructs which may be used in methods of the invention. An optogenetic construct may be an optogenetic red-shift construct, an optogenetic device construct, or an optogenetic enzyme construct as described below.

In an aspect, the present invention provides an optogenetic red-shift construct. An optogenetic red-shift construct of the invention is a polynucleotide sequence encoding a polypeptide, the polypeptide comprising at least one optogenetic device and a retinoid processing enzyme. The optogenetic device may be an optogenetic activator or an optogenetic inhibitor. The present invention also provides isolated polypeptides encoded by optogenetic red-shift constructs, vectors comprising optogenetic red-shift constructs, and isolated cells comprising said vectors.

In another aspect, the present invention provides an optogenetic device construct. An optogenetic device construct of the invention is a polynucleotide sequence encoding a polypeptide, the polypeptide comprising at least one optogenetic device. The optogenetic device may be an optogenetic activator or an optogenetic inhibitor. The present invention also provides isolated polypeptides encoded by optogenetic device constructs, vectors comprising optogenetic device constructs, and isolated cells comprising said vectors.

In still another aspect, the present invention provides an optogenetic enzyme construct. An optogenetic enzyme construct of the invention is a polynucleotide sequence encoding a polypeptide, the polypeptide comprising a retinoid processing enzyme. The present invention also provides isolated polypeptides encoded by optogenetic enzyme constructs, vectors comprising optogenetic enzyme constructs, and isolated cells comprising said vectors.

(a) Polynucleotide Sequence

An optogenetic red-shift construct of the invention is a polynucleotide sequence encoding a polypeptide, the polypeptide comprising at least one optogenetic device and a retinoid processing enzyme. Accordingly, an optogenetic red-shift construct of the invention may be a polynucleotide sequence encoding a polypeptide, the polypeptide comprising 1, 2, 3, 4 or 5 optogenetic devices and a retinoid processing enzyme. Alternatively, an optogenetic red-shift construct of the invention may be a polynucleotide sequence encoding a polypeptide, the polypeptide comprising 1 to 2 optogenetic devices, 1 to 3 optogenetic devices, 1 to 4 optogenetic devices, 1 to 5 optogenetic devices, 2 to 3 optogenetic devices, 2 to 4 optogenetic devices, 2 to 5 optogenetic devices, 3 to 4 optogenetic devices, or 3 to 5 optogenetic devices and a retinoid processing enzyme. One skilled in the art will appreciate that when two or more optogenetic devices are present, each optogenetic device may be the same or different, in any number of combinations. For example, each optogenetic device may be the same optogenetic activator, or the same optogenetic inhibitor, or different optogenetic activators, or different optogenetic inhibitors, or a combination of the same or different optogenetic activators and optogenetic inhibitors.

In the foregoing embodiment, a polynucleotide encoding a polypeptide comprising at least one optogenetic device and retinoid processing enzyme may be operably linked to a single promoter such that one polypeptide is encoded. Alternatively, an optogenetic red-shift construct is a polynucleotide sequence encoding more than one polypeptide, a first polypeptide comprising at least one optogenetic device and a second polypeptide comprising a retinoid processing enzyme. As such, a polynucleotide encoding a polypeptide comprising at least one optogenetic device and retinoid processing enzyme may be operably linked to different promoters such that more than one polypeptide is encoded. In the foregoing embodiment, a polynucleotide encoding a polypeptide comprising at least one optogenetic device may be operably linked to a first promoter and a polynucleotide encoding a polypeptide comprising a retinoid processing enzyme may be operably linked to a second promoter such that more than one polypeptide is encoded. Still further, a polynucleotide encoding a polypeptide comprising a first optogenetic device may be operably linked to a first promoter, a polynucleotide encoding a polypeptide comprising a second optogenetic device may be operably linked to a second promoter, and a polynucleotide encoding a polypeptide comprising a retinoid processing enzyme may be operably linked to a third promoter such that more than one polypeptide is encoded.

When the polynucleotide encoding a polypeptide comprising at least one optogenetic device and retinoid processing enzyme is operably linked to a single promoter, several strategies common in the art may be used to generate more than one polypeptide. For example, a splicing signal may be inserted between the polynucleotide encoding a polypeptide comprising an optogenetic device and the polynucleotide encoding a polypeptide comprising a retinoid processing enzyme, or an internal ribosomal entry site (IRES) may be inserted between the polynucleotide encoding a polypeptide comprising an optogenetic device and the polynucleotide encoding a polypeptide comprising a retinoid processing enzyme, or a proteolytic cleavage site may be inserted between the polynucleotide encoding a polypeptide comprising an optogenetic device and the polynucleotide encoding a polypeptide comprising a retinoid processing enzyme. In each of the foregoing examples, if more than one polynucleotide encoding a polypeptide comprising an optogenetic device is used, a splicing signal, IRES or proteolytic cleavage site may be inserted between each polynucleotide encoding a polypeptide comprising an optogenetic device. The splicing signal, IRES or proteolytic cleavage site inserted between each polynucleotide encoding a polypeptide comprising an optogenetic device and a retinoid processing enzyme may be the same or different.

The splicing signal, IRES or proteolytic cleavage site may be inserted between the C-terminus of the optogenetic device and the N-terminus of the retinoid processing enzyme. Alternatively, the splicing signal, IRES or proteolytic cleavage site may be inserted between the C-terminus of the retinoid processing enzyme and the N-terminus of the optogenetic device. In a specific embodiment, the proteolytic cleavage site may be a self-cleavable linker. A self-cleavable linker may also be referred to as a self-processing peptide. A self-cleavable linker may be a 2A peptide from a virus such as the foot-and-mouth disease virus, equine rhinitis A virus, *Thosea asigna* virus, porcine teschovirus-1, picornaviruses, insect viruses and type C rotaviruses. The average length of 2A peptides is 18-22 amino acids.

In each of the above embodiments, the "optogenetic device" may be as described in detail above in Section I, which is hereby incorporated by reference into this section. In each of the above embodiments, the "retinoid processing enzyme" may be as described in detail above in Section II, which is hereby incorporated by reference into this section.

Preferably, in each of the above embodiments, the optogenetic red-shift construct of the invention is a polynucleotide sequence encoding a polypeptide, wherein the polypeptide comprises at least one optogenetic device that is selected from the group consisting of: (i) channelrhodopsin or derivatives thereof; (ii) halorhodopsin or derivatives thereof; and (iii) channelrhodopsin or derivatives thereof and halorhodopsin or derivatives thereof; and Cyp27c1 as the retinoid processing enzyme, wherein the optogenetic device(s) and retinoid processing enzyme are separated via a self-cleavable linker.

An optogenetic device construct of the invention is a polynucleotide sequence encoding a polypeptide, the polypeptide comprising at least one optogenetic device. Accordingly, an optogenetic device construct of the invention may be a polynucleotide sequence encoding a polypeptide, the polypeptide comprising 1, 2, 3, 4 or 5 optogenetic devices. Alternatively, an optogenetic device construct of the invention may be a polynucleotide sequence encoding a polypeptide, the polypeptide comprising 1 to 2 optogenetic devices, 1 to 3 optogenetic devices, 1 to 4 optogenetic devices, 1 to 5 optogenetic devices, 2 to 3 optogenetic devices, 2 to 4 optogenetic devices, 2 to 5 optogenetic devices, 3 to 4 optogenetic devices, or 3 to 5 optogenetic devices. One skilled in the art will appreciate that when two or more optogenetic devices are present, each optogenetic device may be the same or different, in any number of combinations. For example, each optogenetic device may be the same optogenetic activator, or the same optogenetic inhibitor, or different optogenetic activators, or different optogenetic inhibitors, or a combination of the same or different optogenetic activators and optogenetic inhibitors.

In the foregoing embodiment, a polynucleotide encoding a polypeptide comprising at least one optogenetic device may be operably linked to a single promoter such that one polypeptide is encoded. Alternatively, an optogenetic device construct is a polynucleotide sequence encoding more than one polypeptide, a first polypeptide comprising a first optogenetic device and a second polypeptide comprising a second optogenetic device. As such, a polynucleotide encoding a polypeptide comprising a first optogenetic device and a second optogenetic device may be operably linked to different promoters such that more than one polypeptide is encoded. In the foregoing embodiment, a polynucleotide encoding a polypeptide comprising a first optogenetic device may be operably linked to a first promoter and a polynucleotide encoding a polypeptide comprising a second optogenetic device may be operably linked to a second promoter, and so on such that more than one polypeptide is encoded.

When the polynucleotide encoding a polypeptide comprising more than one optogenetic device is operably linked to a single promoter, several strategies common in the art may be used to generate more than one polypeptide. For example, a splicing signal may be inserted between the polynucleotide encoding a polypeptide comprising a first optogenetic device and the polynucleotide encoding a polypeptide comprising a second optogenetic device, or an internal ribosomal entry site (IRES) may be inserted between the polynucleotide encoding a polypeptide comprising a first optogenetic device and the polynucleotide encoding a polypeptide comprising a second optogenetic device, or a proteolytic cleavage site may be inserted between the polynucleotide encoding a polypeptide comprising a first optogenetic device and the polynucleotide encoding a polypeptide comprising a second optogenetic device. The splicing signal, IRES or proteolytic cleavage site inserted between each polynucleotide encoding a polypeptide may be the same or different.

In a specific embodiment, the proteolytic cleavage site may be a self-cleavable linker. A self-cleavable linker may also be referred to as a self-processing peptide. A self-cleavable linker may be a 2A peptide from a virus such as the foot-and-mouth disease virus, equine rhinitis A virus, *Thosea asigna* virus, porcine teschovirus-1, picornaviruses, insect viruses and type C rotaviruses. The average length of 2A peptides is 18-22 amino acids.

In each of the above embodiments, the "optogenetic device" may be as described in detail above in Section I, which is hereby incorporated by reference into this section. Preferably, in each of the above embodiments, the optogenetic device construct of the invention is a polynucleotide sequence encoding a polypeptide, wherein the polypeptide comprises at least one optogenetic device that is selected from the group consisting of: (i) channelrhodopsin or derivatives thereof; (ii) halorhodopsin or derivatives thereof; and (iii) channelrhodopsin or derivatives thereof and halorhodopsin or derivatives thereof separated via a self-cleavable linker.

An optogenetic enzyme construct of the invention is a polynucleotide sequence encoding a polypeptide, the polypeptide comprising a retinoid processing enzyme. The "retinoid processing enzyme" may be as described in detail above in Section II, which is hereby incorporated by reference into this section. Preferably, the optogenetic enzyme construct of the invention is a polynucleotide sequence encoding a polypeptide, wherein the polypeptide comprises Cyp27c1 as the retinoid processing enzyme.

Polynucleotide sequences of the invention may be produced from nucleic acids molecules using molecular biological methods known to in the art. Any of the methods known to one skilled in the art for the amplification of polynucleotide fragments and insertion of polynucleotide fragments into a vector may be used to construct the polynucleotide sequences of the invention. These methods may include in vitro recombinant DNA and synthetic techniques and in vivo recombinations (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

(b) Polypeptide Sequence

In another aspect, the present invention provides one or more isolated polypeptide(s) encoded by a polynucleotide sequence of the invention. Polynucleotide sequences of the invention are described in detail in Section III(a), and are hereby incorporated by reference into this section. In an embodiment, an isolated polypeptide of the invention comprises an optogenetic device. In another embodiment, an isolated polypeptide of the invention comprises a retinoid processing enzyme. In still another embodiment, an isolated polypeptide of the invention comprises an optogenetic device linked to a retinoid processing enzyme. In such an embodiment, an isolated polypeptide may comprise an optogenetic device attached to a retinoid processing enzyme via a linker stretching between the C-terminus of the optogenetic device to the N-terminus of the retinoid processing enzyme. Alternatively, an isolated polypeptide may comprise an optogenetic device attached to a retinoid processing enzyme via a linker stretching between the C-terminus of the retinoid processing enzyme to the N-terminus of the optogenetic device. The optogenetic device and retinoid processing enzyme may be separated via cleavage before or after isolation of the polypeptide.

Isolated polypeptides of the invention may be produced from nucleic acids molecules using molecular biological methods known to in the art. Generally speaking, a polynucleotide sequence encoding the polypeptide is inserted into a vector that is able to express the polypeptide when introduced into an appropriate host cell. Appropriate host cells include, but are not limited to, bacterial, yeast, insect, and mammalian cells. Once expressed, polypeptides may be obtained from cells of the invention using common purification methods. For example, if the polypeptide has a secretion signal, expressed polypeptides may be isolated from cell culture supernatant. Alternatively, polypeptides lacking a secretion signal may be purified from inclusion bodies and/or cell extract. Polypeptides of the invention may be isolated from culture supernatant, inclusion bodies or cell extract using any methods known to one of skill in the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Isolation of polypeptides is greatly aided when the polypeptide comprises a purification moiety.

(c) Vector

In another aspect, the present invention provides a vector comprising an optogenetic construct of the invention. As used herein, a vector is defined as a nucleic acid molecule used as a vehicle to transfer genetic material. Vectors include but are not limited to, plasmids, phasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

The vector may have a high copy number, an intermediate copy number, or a low copy number. The copy number may be utilized to control the expression level for the optogenetic device and/or retinoid processing enzyme, and as a means to control the expression vector's stability. In one embodiment, a high copy number vector may be utilized. A high copy number vector may have at least 31, 35, 40, 45, 50, 55, 60, 65, 70, 75, 80, 85, 90, 95, or 100 copies per bacterial cell. In other embodiments, the high copy number vector may have at least 100, 125, 150, 175, 200, 225, 250, 275, 300, 325, 350, 375, or 400 copies per host cell. In an alternative embodiment, a low copy number vector may be utilized. For example, a low copy number vector may have one or at least two, three, four, five, six, seven, eight, nine, or ten copies per host cell. In another embodiment, an intermediate copy number vector may be used. For instance, an intermediate copy number vector may have at least 10, 11, 12, 13, 14, 15, 16, 17, 18, 19, 20, 21, 22, 23, 24, 25, 26, 27, 28, 29, or 30 copies per host cell.

Expression vectors typically contain one or more of the following elements: promoters, terminators, ribosomal binding sites, and IRES. Promoters that allow expression in all cell types such as constitutive promoters (e.g. CBA/CAGGS/ACTB, CAG, CMV, UBC, EF1α, SV40, PGK, CBh, MeCP2, U6 and H1) could be utilized. In addition cell type specific promoters for neurons (e.g. syapsin, SYN1, NSE/RU5'), neuroendocrine cells (e.g. chromogranin A), muscle cells (e.g. desmin, Mb), or cardiomyocytes (e.g. alpha myosin heavy-chain promoter) could be used. In order to target expression to retinal photoreceptors the CRX, IRBP, Rhodopsin, blue cone opsin, or red cone opsin promoters could be used. In exemplary embodiments, the pan-bipolar promoter Chx10 may be used. In another exemplary embodiment, the Omp promoter may be used.

Expression of the nucleic acid molecules of the invention may be regulated by a second nucleic acid sequence so that the molecule is expressed in a host transformed with the recombinant DNA molecule. For example, expression of the nucleic acid molecules of the invention may be controlled by any promoter/enhancer element known in the art.

A nucleic acid encoding an optogenetic device and/or retinoid processing enzyme may also be operably linked to a nucleotide sequence encoding a selectable marker. A selectable marker may be used to efficiently select and identify cells that have integrated the exogenous nucleic acids. Selectable markers give the cell receiving the exogenous nucleic acid a selection advantage, such as resistance towards a certain toxin or antibiotic. Suitable examples of antibiotic resistance markers include, but are not limited to, those coding for proteins that impart resistance to kanamycin, spectomycin, neomycin, gentamycin (G418), ampicillin, tetracycline, chloramphenicol, puromycin, hygromycin, zeocin, and blasticidin.

In some embodiments, the vector may also comprise a transcription cassette for expressing reporter proteins. By way of example, reporter proteins may include a fluorescent protein, luciferase, alkaline phosphatase, beta-galactosidase, beta-lactamase, horseradish peroxidase, and variants thereof.

An expression vector encoding optogenetic device and/or retinoid processing enzyme may be delivered to the cell using a viral vector or via a non-viral method of transfer. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. An expression construct encoding an optogenetic device and/or retinoid processing enzyme that is introduced to the cell may be linear or circular, may be single-stranded or double-stranded, and may be DNA, RNA, or any modification or combination thereof.

An expression construct encoding an optogenetic device and/or retinoid processing enzyme may be introduced into the cell by transfection. Methods for transfecting nucleic acids are well known to persons skilled in the art. Transfection methods include, but are not limited to, viral transduction, cationic transfection, liposome transfection, dendrimer transfection, electroporation, heat shock, nucleofection transfection, magnetofection, nanoparticles, biolistic particle delivery (gene gun), and proprietary transfection reagents such as Lipofectamine, Dojindo Hilymax, Fugene, jetPEI, Effectene, or DreamFect.

Upon introduction into the cell, an expression construct encoding an optogenetic device and/or retinoid processing enzyme may be integrated into a chromosome. In some embodiments, integration of the expression construct encoding an optogenetic device and/or retinoid processing enzyme into a cellular chromosome may be achieved with a mobile element. The mobile element may be a transposon or a retroelement. A variety of transposons are suitable for use in the invention. Examples of DNA transposons that may be used include the Mu transposon, the P element transposons from *Drosophila*, and members of the Tc1/Mariner superfamily of transposons such as the sleeping beauty transposon from fish. A variety of retroelements are suitable for use in the invention and include LTR-containing retrotransposons and non-LTR retrotransposons. Non-limiting examples of retrotransposons include Copia and gypsy from *Drosophila melanogaster*, the Ty elements from *Saccharomyces cerevisiae*, the long interspersed elements (LINEs), and the short interspersed elements (SINEs) from eukaryotes. Suitable examples of LINEs include L1 from mammals and R2Bm from silkworm.

Integration of the exogenous nucleic acid into a cellular chromosome may also be mediated by a virus. Viruses that integrate nucleic acids into a chromosome include retroviruses. A variety of retroviruses are suitable for use in the invention. Retroviral vectors may either be replication-competent or replication-defective. The retroviral vector may be an alpharetrovirus, a betaretrovirus, a gammaretrovirus, a deltaretrovirus, an epsilonretrovirus, a lentivirus, or a spumaretrovirus. In an embodiment, the retroviral vector may be a lentiviral vector. The lentiviral vector may be derived from human, simian, feline, equine, bovine, or lentiviruses that infect other mammalian species. Non-limiting examples of suitable lentiviruses includes human immunodeficiency virus (HIV), simian immunodeficiency virus (SIV), feline immunodeficiency virus (FIV), bovine immunodeficiency virus (BIV), and equine infectious anemia virus (EIAV).

Integration of an expression construct encoding an optogenetic device and/or retinoid processing enzyme into a chromosome of the cell may be random. Alternatively, integration of an expression construct encoding an optogenetic device and/or retinoid processing enzyme may be targeted to a particular sequence or location of a chromosome. In general, the general environment at the site of integration may affect whether the integrated expression construct encoding an optogenetic device and/or retinoid processing enzyme is expressed, as well as its level of expression.

The virus may be altered to have tropism for a specific cell type. For example, the virus may be altered to have tropism for a muscle cell, a neuroendocrine cell, or a neuron. Specifically, the virus may be altered to have tropism for retinal biopolar cells or retinal ganglion cells.

Cells transfected with the expression construct encoding an optogenetic device and/or retinoid processing enzyme generally will be grown under selection to isolate and expand cells in which the nucleic acid has integrated into a chromosome. Cells in which the expression construct encoding an optogenetic device and/or retinoid processing enzyme has been chromosomally integrated may be maintained by continuous selection with the selectable marker as described above. The presence and maintenance of the integrated exogenous nucleic acid sequence may be verified using standard techniques known to persons skilled in the art such as Southern blots, amplification of specific nucleic acid sequences using the polymerase chain reaction (PCR), and/or nucleotide sequencing.

Nucleic acid molecules are inserted into a vector that is able to express the fusion polypeptides when introduced into an appropriate host cell. Appropriate host cells include, but are not limited to, bacterial, yeast, insect, and mammalian cells.

In preferred embodiments, a vector-comprising an optogenetic device and/or retinoid processing enzyme of the invention is an adeno-associated viral (AAV) vector. Adeno-associated virus (AAV) vectors may be from human or nonhuman primate AAV serotypes and variants thereof. Suitable adeno-associated viruses include AAV type 1, AAV type 2, AAV type 3, AAV type 4, AAV type 5, AAV type 6, AAV type 7, AAV type 8, AAV type 9, AAV type 10, and AAV type 11. Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J Virol*, 45: 555-564 (1983) as corrected by Ruffing et al., *J Gen Virol*, 75: 3385-3392 (1994). Cis-acting sequences directing viral DNA replication, encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus, making cold preservation of AAV less critical. AAV may even be lyophilized. Finally, AAV-infected cells are not resistant to superinfection.

Multiple serotypes of AAV exist and offer varied tissue tropism. Known serotypes include, for example, AAV1, AAV2, AAV3, AAV4, AAV5, AAV6, AAV7, AAV8, AAV9, AAV10 and AAV11. AAV9 is described in U.S. Pat. No. 7,198,951 and in Gao et al., *J. Virol.*, 78: 6381-6388 (2004). Advances in the delivery of AAV6 and AAV8 have made possible the transduction by these serotypes of skeletal and cardiac muscle following simple systemic intravenous or intraperitoneal injections. See, Pacak et al., *Circ. Res.*, 99(4): 3-9 (1006) and Wang et al., *Nature Biotech.*, 23(3): 321-328 (2005). The use of some serotypes of AAV to target cell types within the central nervous system, though, has required surgical intraparenchymal injection. See, Kaplitt et al., Lancet 369: 2097-2105 (2007); Marks et al., Lancet Neurol 7: 400-408 (2008); and Worgall et al., Hum Gene Ther (2008).

An adeno-associated viral (AAV) vector is a plasmid comprising a recombinant AAV genome. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Production of pseudotyped rAAV is disclosed in, for example, WO 01/83692 which is incorporated by reference herein in its entirety. In an exemplary embodiment, a vector is based on the AAV2 serotype. In another exemplary embodiment, a vector is based on the AAV9 serotype (see, for example, Foust et al., *Nature Biotechnology*, 27: 59-65 (2009); Duque et al., *Mol. Ther.* 17: 1187-1196 (2009); Zincarelli et al., *Mol. Ther.*, 16: 1073-1080 (2008); and U.S. Patent Publication No. 20130039888).

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. No. 5,786,211; U.S. Pat. No. 5,871,982; and U.S. Pat. No. 6,258,595. The foregoing documents are hereby incorporated by reference in their entirety herein, with particular emphasis on those sections of the documents relating to rAAV production.

The invention thus provides packaging cells that produce infectious rAAV. In another aspect, the invention provides rAAV (i.e., infectious encapsidated rAAV particles) comprising a rAAV genome of the invention. In some embodiments of the invention, the rAAV genome is a self-complementary genome.

(d) Isolated Cell

In another aspect, the present invention provides an isolated cell comprising a vector of the invention. The cell may be a prokaryotic cell or a eukaryotic cell. Appropriate cells include, but are not limited to, bacterial, yeast, insect, and mammalian cells.

In some embodiments, the isolated host cell comprising a vector of the invention may be used to produce a polypeptide encoded by an optogenetic construct of the invention. Generally, production of a polypeptide or polypeptides of the invention involves transfecting isolated host cells with a vector comprising an optogenetic construct and then culturing the cells so that they transcribe and translate the desired polypeptide. The isolated host cells may then be lysed to extract the expressed polypeptide for subsequent purification. "Isolated host cells" according to the invention are cells which have been removed from an organism and/or are maintained in vitro in substantially pure cultures. A wide variety of cell types can be used as isolated host cells of the invention, including both prokaryotic and eukaryotic cells. Isolated cells include, without limitation, bacterial cells, fungal cells, yeast cells, insect cells, and mammalian cells.

In one embodiment, the isolated host cell is characterized in that after transformation with a vector of the invention, it produces the desired polypeptide for subsequent purification. Such a system may be used for protein expression and purification as is standard in the art. In some embodiments, the host cell is a prokaryotic cell. Non-limiting examples of suitable prokaryotic cells include *E. coli* and other Enterobacteriaceae, *Escherichia* sp., *Campylobacter* sp., *Wolinella* sp., *Desulfovibrio* sp. *Vibrio* sp., *Pseudomonas* sp. *Bacillus* sp., *Listeria* sp., *Staphylococcus* sp., *Streptococcus* sp., *Peptostreptococcus* sp., *Megasphaera* sp., *Pectinatus* sp., *Selenomonas* sp., *Zymophilus* sp., *Actinomyces* sp., *Arthrobacter* sp., *Frankia* sp., *Micromonospora* sp., *Nocardia* sp., *Propionibacterium* sp., *Streptomyces* sp., *Lactobacillus* sp., *Lactococcus* sp., *Leuconostoc* sp., *Pediococcus* sp., *Acetobacterium* sp., *Eubacterium* sp., *Heliobacterium* sp., *Heliospirillum* sp., *Sporomusa* sp., *Spiroplasma* sp., *Ureaplasma* sp., *Erysipelothrix* sp., *Corynebacterium* sp. *Enterococcus* sp., *Clostridium* sp., *Mycoplasma* sp., *Mycobacterium* sp., *Actinobacteria* sp., *Salmonella* sp., *Shigella* sp., *Moraxella* sp., *Helicobacter* sp, *Stenotrophomonas* sp., *Micrococcus* sp., *Neisseria* sp., *Bdellovibrio* sp., *Hemophilus* sp., *Klebsiella* sp., *Proteus mirabilis*, *Enterobacter cloacae*, *Serratia* sp., *Citrobacter* sp., *Proteus* sp., *Serratia* sp., *Yersinia* sp., *Acinetobacter* sp., *Actinobacillus* sp. *Bordetella* sp., *Brucella* sp., *Capnocytophaga* sp., *Cardiobacterium* sp., *Eikenella* sp., *Francisella* sp., *Haemophilus* sp., *Kingella* sp., *Pasteurella* sp., *Flavobacterium* sp. *Xanthomonas* sp., *Burkholderia* sp., *Aeromonas* sp., *Plesiomonas* sp., *Legionella* sp. and alpha-proteobaeteria such as *Wolbachia* sp., cyanobacteria, spirochaetes, green sulfur and green nonsulfur bacteria, Gram-negative cocci, Gram negative bacilli which are fastidious, Enterobacteriaceae-glucose-fermenting gram-negative bacilli, Gram negative bacilli-non-glucose fermenters, Gram negative bacilli-glucose fermenting, oxidase positive.

Particularly useful bacterial host cells for protein expression include Gram negative bacteria, such as *Escherichia coli, Pseudomonas fluorescens, Pseudomonas haloplanctis, Pseudomonas putida* AC10, *Pseudomonas pseudoflava, Bartonella henselae, Pseudomonas syringae, Caulobacter crescentus, Zymomonas mobilis, Rhizobium meliloti, Myxococcus xanthus* and Gram positive bacteria such as *Bacillus subtilis, Corynebacterium, Streptococcus cremoris, Streptococcus lividans*, and *Streptomyces lividans*. *E. coli* is one of the most widely used expression hosts. Accordingly, the techniques for overexpression in *E. coli* are well developed and readily available to one of skill in the art. Further, *Pseudomonas fluorescens*, is commonly used for high level production of recombinant proteins (i.e. for the development bio-therapeutics and vaccines).

Particularly useful fungal host cells for protein expression include *Aspergillis oryzae, Aspergillis niger, Trichoderma reesei, Aspergillus nidulans, Fusarium graminearum*. Particularly useful yeast host cells for protein expression include *Candida albicans, Candida maltose, Hansenula polymorpha, Kluyveromyces fragilis, Kluyveromyces lactis, Pichia guillerimondii, Pichia pastoris, Saccharomyces cerevisiae, Schizosaccharomyces pombe*, and *Yarrowia lipolytica*.

Particularly useful mammalian host cells for protein expression include Chinese hamster ovary (CHO) cells, HeLa cells, baby hamster kidney (BHK) cells, monkey kidney cells (COS), human hepatocellular carcinoma cells (eg. Hep G2), human embryonic kidney cells, *Bos primigenius*, and *Mus musculus*. Additionally, the mammalian host cell may be an established, commercially-available cell line (e.g., American Type Culture Collection (ATCC), Manassas, Va.). The host cell may be an immortalized cell. Alternatively, the host cell may be a primary cell. "Primary cells" are cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

In another embodiment, the host cell may be in vivo; i.e., the cell may be disposed in a subject. Accordingly, a polypeptide of the invention is expressed from a host cell in the subject. In certain embodiments, a host cell in a subject may be selected from the group consisting of muscle cells, neuroendocrine cells and neurons. In a specific embodiment, the host cell may be neuron. In an exemplary embodiment, an AAV vector may be used to express a polypeptide of the invention in a host cell disposed in a subject.

IV. Methods

Another aspect of the present invention encompasses methods utilizing an optogenetic construct described in Section III above.

In one embodiment, the invention encompasses a method of red-shifting the activation wavelength of an optogenetic device in a subject. The method comprises administering a composition comprising a vector, the vector comprising an optogenetic red-shift construct of the invention. In a specific embodiment, the method comprises administering a composition comprising a rAAV, the rAAV comprising an optogenetic red-shift construct of the invention. In preferred embodiments, the optogenetic red-shift construct is a polynucleotide sequence encoding a polypeptide comprising at least one optogenetic device and a retinoid processing enzyme.

In another embodiment, the invention encompasses a method of depolarizing an electrically active cell. The method comprises administering to the cell a composition comprising a vector, the vector comprising an optogenetic red-shift construct of the invention, wherein the optogenetic red-shift construct comprises an optogenetic activator. In a specific embodiment, the method comprises administering to the cell a composition comprising a rAAV, the rAAV comprising an optogenetic red-shift construct of the invention. In preferred embodiments, the optogenetic red-shift construct is a polynucleotide sequence encoding a polypeptide comprising at least one optogenetic activator and a retinoid processing enzyme.

In still another embodiment, the invention encompasses a method of hyperpolarizing an electrically active cell. The method comprises administering to the cell a composition comprising a vector, the vector comprising an optogenetic red-shift construct of the invention, wherein the optogenetic red-shift construct comprises an optogenetic inhibitor. In a specific embodiment, the method comprises administering to the cell a composition comprising a rAAV, the rAAV comprising an optogenetic red-shift construct of the invention. In preferred embodiments, the optogenetic red-shift construct is a polynucleotide sequence encoding a polypeptide comprising at least one optogenetic inhibitor and a retinoid processing enzyme.

In yet another embodiment, the invention encompasses a method of red-shifting the activation wavelength of an optogenetic device in a subject. The method comprises co-administering a composition comprising a first vector, the first vector comprising an optogenetic device construct of the invention and a composition comprising a second vector, the second vector comprising an optogenetic enzyme construct of the invention. In preferred embodiments, the optogenetic device construct is a polynucleotide sequence encoding a polypeptide comprising at least one optogenetic device and the optogenetic enzyme construct is a polynucleotide sequence encoding a polypeptide comprising a retinoid processing enzyme. Alternatively, in place of a composition comprising a second vector, a composition comprising an isolated protein comprising a retinoid processing enzyme may be co-administered.

In a different embodiment, the invention encompasses a method of depolarizing an electrically active cell. The method comprises co-administering to the cell a composition comprising a first vector, the first vector comprising an optogenetic device construct of the invention and a composition comprising a second vector, the second vector comprising an optogenetic enzyme construct of the invention. In preferred embodiments, the optogenetic device construct is a polynucleotide sequence encoding a polypeptide comprising at least one optogenetic activator and the optogenetic enzyme construct is a polynucleotide sequence encoding a polypeptide comprising a retinoid processing enzyme. Alternatively, in place of a composition comprising a second vector, a composition comprising an isolated protein comprising a retinoid processing enzyme may be co-administered.

In still another embodiment, the invention encompasses a method of hyperpolarizing an electrically active cell. The method comprises co-administering to the cell a composition comprising a first vector, the first vector comprising an optogenetic device construct of the invention and a composition comprising a second vector, the second vector comprising an optogenetic enzyme construct of the invention. In preferred embodiments, the optogenetic device construct is a polynucleotide sequence encoding a polypeptide comprising at least one optogenetic inhibitor and the optogenetic enzyme construct is a polynucleotide sequence encoding a polypeptide comprising a retinoid processing enzyme. Alternatively, in place of a composition comprising a second vector, a composition comprising an isolated protein comprising a retinoid processing enzyme may be co-administered.

In certain aspects, the method comprises co-administering a composition comprising three vectors, wherein a first vector comprises a polynucleotide sequence encoding a polypeptide comprising an optogenetic activator of the invention, a second vector comprises a polynucleotide sequence encoding a polypeptide comprising a retinoid processing enzyme of the invention, and a third vector comprises a polynucleotide sequence encoding a polypeptide comprising an optogenetic inhibitor of the invention.

For the above embodiments, the phrase "co-administering" encompasses any form of administration that allows the functioning of both the optogenetic device and the retinoid processing enzyme to the cell or tissue of interest. Suitable methods include those known to deliver a nucleic acid to a cell. "Co-administering" encompasses both a situation where the vector comprising an optogenetic device construct of the invention and the vector comprising a retinoid processing enzyme or isolated protein comprising a retinoid processing enzyme are administered simultaneously, optionally in the same composition, and situations where the vector comprising an optogenetic device and the vector comprising a retinoid processing enzyme or isolated protein comprising a retinoid processing enzyme are administered sequentially. If the vector comprising an optogenetic device and the vector comprising a retinoid processing enzyme or isolated protein comprising a retinoid processing enzyme are administered sequentially, the second vector or protein to be administered is administered before the concentration of the first vector decreases below effective levels. For instance, depending on the first vector, the second vector or protein may be administered minutes, hours, days, or weeks after the first vector.

A first vector and a second vector may be co-administered at varying ratios, for example, in a 1:1 ratio. Alternatively, a first vector and a second vector may be co-administered at a ratio of about 2:1, about 3:1, about 4:1, about 5:1, about 6:1, about 7:1, about 8:1, about 9:1 or about 10:1. Additionally, a first vector and a second vector may be co-administered at a ratio of about 20:1, about 50:1 or about 100:1. In another embodiment, a second vector and a first vector may be co-administered at a ratio of about 2:1, about 3:1, about 4:1, about 5:1, about 6:1, about 7:1, about 8:1, about 9:1 or about 10:1.

When administering a composition comprising an rAAV, one of skill in the art will appreciate that the method of the administration will vary depending, for example, on the particular rAAV and the cell type(s) being targeted, and may be determined by methods standard in the art. Titers of rAAV may range from about $1 \times 10^6$, about $1 \times 10^7$, about $1 \times 10^8$, about $1 \times 10^9$, about $1 \times 10^{10}$, about $1 \times 10^{11}$, about $1 \times 10^{12}$, about $1 \times 10^{13}$ to about $1 \times 10^{14}$ or more DNase resistant particles (DRP) per ml. Dosages may also be expressed in units of viral genomes (vg). Dosages may also vary based on the timing of the administration to a human. These dosages of rAAV may range from about $1 \times 10^{11}$ vg/kg, about $1 \times 10^{12}$, about $1 \times 10^{13}$, about $1 \times 10^{14}$, about $1 \times 10^{15}$, about $1 \times 10^{16}$ or more viral genomes per kilogram body weight in an adult. For a neonate, the dosages of rAAV may range from about $1 \times 10^{11}$, about $1 \times 10^{12}$, about $3 \times 10^{12}$, about $1 \times 10^{13}$, about $3 \times 10^{13}$, about $1 \times 10^{14}$, about $3 \times 10^{14}$, about $1 \times 10^{15}$, about $3 \times 10^{15}$, about $1 \times 10^{16}$, about $3 \times 10^{16}$ or more viral genomes per kilogram body weight.

In each of the above embodiments, a composition may further comprise an excipient. Non-limiting examples of excipients include antioxidants, binders, buffers, diluents (fillers), disintegrants, dyes, effervescent disintegration agents, preservatives (antioxidants), flavor-modifying agents, lubricants and glidants, dispersants, coloring agents, pH modifiers, chelating agents, preservatives (e.g., antibacterial agents, antifungal agents), release-controlling polymers, solvents, surfactants, and combinations of any of these agents. Cells are contacted with the composition comprising a vector or protein of the invention under effective conditions for a period of time sufficient to deliver an optogenetic construct to a cell. In certain embodiments, the goal may be to deliver an optogenetic construct to a cell of a subject. The subject's cell may be isolated, or the optogenetic construct may be delivered to the cell in the subject. When the subject's cell is not isolated, the composition may be administered to the subject orally, parenteraly, intraperitoneally, intravascularly, intrapulmonary, topically, intravitreally, or subretinally. The term parenteral as used herein includes subcutaneous, intravenous, intramuscular, intrathecal, or intrasternal injection, or infusion techniques. In a specific embodiment, the composition may be administered intravitreally or subretinally.

As used herein, an "electrically active cell" is a cell whose function is determined by the generation or the reception of an electric signal. For example, an electrically active cell may include, but is not limited to, a muscle cell, a neuroendocrine cell, or a neuron. Non-limiting examples of a muscle cell may include a cardiac muscle cell, an internodal tract myocyte, a myocyte of atrioventricular node, a myocte of sinoatrial node, a myocyte, a non-striated muscle cell, an obliquely striated muscle cell, a skeletal muscle fiber, a somatic muscle cell, a striated muscle cell, or a visceral muscle cell. Non-limiting examples of a neuroendocrine cell may include an APUD cell, a Feyrter cell, a lung neuroendocrine cell, a paraganglial type 1 cell, or a stomach neuroendocrine cell. Non-limiting examples of a neuron may include a CNS neuron, a GABAergic neuron, an afferent neuron, an autonomic neuron, a cerebellar neuron, a cerebral cortex neuron, a chemoreceptor cell, a cholinergic neuron, an efferent neuron, an interneuron, an adrenergic neuron, a cardiac neuron, a columnar neuron, a commissural neuron, a dopaminergic neuron, an enteric neuron, a galanergic neuron, a glutamatergic neuron, a glycinergic neuron, a gonatodropin releasing neuron, a hypocretin-secreting neuron, a kidney nerve cell, a lateral ventricle neuron, a magnocellular neurosecretory cell, a mechanoreceptor cell, a neuron neural crest derived, a neuronal receptor cell, an olfactory receptor cell, a photoreceptor cell, a retinal bipolar cell, a retinal ganglion cell, a primary neuron, a secondary neuron, a taste receptor cell, a histaminergic neuron, a medium spiny neuron, a multipolar neuron, a nitrergic neuron, a olfactory bulb tufted cell, a peptidergic neuron, a peripheral neuron, a pioneer neuron, a polymodal neuron, a posterior lateral line ganglion neuron, a pseudounipolar neuron, a retrotrapezoid nucleus neuron, a sensory processing neuron, a serotonergic neuron, a smooth muscle cell of sigmoid colon, a spiral ganglion neuron, a touch receptor cell, or a unipolar neuron. In a specific embodiment, an electrically active cell may be a retinal bipolar cell or a retinal ganglion cell.

As used herein, "depolarizing" is a change in a cell's membrane potential that makes it more positive. Depolarization may make an action potential more likely to occur.

As used herein, "hyperpolarizing" is a change in a cell's membrane potential that makes it more negative. Hyperpolarization inhibits action potentials by increasing the stimulus required to move the membrane potential to the action potential threshold.

The invention encompasses a method of red-shifting the activation wavelength of an optogenetic device in a subject. According to the invention, the addition of a retinoid processing enzyme with an optogenetic device may shift the sensitivity of the optogenetic device toward the red end of the light spectrum. Thus, as used herein, "red-shift" means that the overall sensitivity of the optogenetic device is shifted toward the red end of the spectrum. Such shifts are also referred to as "bathochromic" shifts. A skilled artisan would understand that the magnitude of the shift may depend upon the specific optogenetic device used. Accordingly, the sensitivity of the optogenetic device may be shifted by about 30 nm or more. In another embodiment, the sensitivity of the optogenetic device may be shifted by about 10, about 20, about 30, about 40, or about 50 nm. In yet another embodiment, the sensitivity of the optogenetic device may be shifted by about 60, about 70, about 80, about 90 or about 100 nm. For example, the sensitivity of the optogenetic device may be shifted by about 10, 11, 12, 13, 14 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 4 or 50 nm. In an exemplary embodiment, the sensitivity of the optogenetic device is shifted by 30 nm or more.

(a) Tissue

In still yet another embodiment, the invention encompasses a method of extending tissue depth at which an optogenetic device can function. The method comprises administering a composition comprising a vector, the vector comprising an optogenetic red-shift construct of the invention. The method further comprises administering light to the tissue, and measuring the function of the optogenetic device, wherein function of the optogenetic device co-expressed with the retinoid processing enzyme is measured at a depth greater than the function of an optogenetic device alone. Alternatively, the method comprises co-administering a composition comprising a first vector, the first vector comprising an optogenetic device construct of the invention and a composition comprising a second vector, the second vector comprising an optogenetic enzyme construct of the invention A suitable tissue for the invention may be a tissue that can receive a vector of the invention. Non-limiting examples of tissue suitable for the invention may include, brain, heart, eye, liver, lung, skin, kidney, muscle, nerve, spleen, and bowel. In an exemplary embodiment, a tissue of the invention may be heart, eye, or brain tissue.

A method of the invention further comprises administering light to the tissue. According to the invention, the optogenetic device may be activated with light that is shifted toward the red end of the spectrum (i.e. has a longer wavelength) relative to the wavelength of light that the optogenetic device responds to in absence of a retinoid processing enzyme. In a specific embodiment, the optogenetic device, in the presence of the retinoid processing enzyme, may be activated by red, far red, or infrared light. The ability to activate the optogenetic device with light with a longer wavelength has the added benefit of increasing the depth of tissue penetration because longer wavelength light can penetrate tissue more readily. This benefit has important implications for optogenetics-based therapies in the large human brain and in human cardiac tissue which is highly opaque to shorter wavelength light. The ability to apply longer wavelength light, such as far red light, may allow increase activation of an optogenetic device. Methods to activate optogenetic devices with light are known in the art. For example, light may be projected onto the tissue. Specifically, light may projected onto the retina, the brain, or the heart. A monochromatic light source may be used to provide a light, light flashes, or periodic light pulses at defined wavelengths. Light may be applied at a wavelength at which the optogenetic device is activated. For example, light may be applied at a wavelength greater than 495 nm, or greater than 570 nm, or greater than 590 nm, or greater than 620 nm. In an embodiment, light may be applied at a wavelength of about 495 nm to about 570 nm. In another embodiment, light may be applied at a wavelength of about 570 nm to about 590 nm. In still another embodiment, light may be applied at a wavelength of about 590 nm to about 620 nm. In yet still another embodiment, light may be applied at a wavelength of about 620 nm to about 750 nm. In a further another embodiment, light may be applied at a wavelength of about 710 nm to about 850 nm. In a different embodiment, light may be applied at a wavelength of about 700 nm to about 1050 nm. In a specific embodiment, light may be applied at a wavelength of greater than 620 nm.

The function of the optogenetic device may be measured by evaluating tissue activity. For example, if the tissue is neural tissue (i.e. brain or retina), the function of the optogenetic device may be measured by recording the activity of neurons in the tissue. In another example, if the tissue is cardiac tissue, the function of the optogenetic device may be measured by recording the activity of the cardiomyocytes in the tissue. In yet another example, if the tissue is eye tissue, the function of the optogenetic device may be measured by recording electrical activity.

The depth of the function of the optogenetic device may be measured by determining the level of activation of the tissue. For example, if the depth of function of the optogenetic device is minimal, the level of function of the tissue will be minimal. According to the invention, the depth of function of the optogenetic device when co-expressed with a retinoid processing enzyme may be greater than the depth of function of an optogenetic device alone. In an embodiment, the depth of function of the optogenetic device when co-expressed with a retinoid processing enzyme may be about 1.5 fold, about 2 fold, about 2.5 fold, about 3 fold, about 3.5 fold, about 4 fold, about 4.5 fold, or about 5 fold greater than the depth of function of an optogenetic device alone. In another embodiment, the depth of function of the optogenetic device when co-expressed with a retinoid processing enzyme may be about 6 fold, about 7 fold, about 8 fold, about 9 fold, or about 10 fold greater than the depth of function of an optogenetic device alone. In yet another embodiment, the depth of function of the optogenetic device when co-expressed with a retinoid processing enzyme may be about 20 fold, about 30 fold, about 40 fold, about 50 fold, about 60 fold, about 70 fold, about 80 fold, or about 100 fold greater than the depth of function of an optogenetic device alone.

(b) Visual

In another aspect, the present disclosure encompasses a method of restoring sensitivity to light in an inner retinal cell. The method comprises administering to the cell a composition comprising a vector, the vector comprising an optogenetic red-shift construct of the invention. Alternatively, the method comprises co-administering to the cell a composition comprising a first vector, the first vector comprising an optogenetic device construct of the invention and a composition comprising a second vector, the second vector comprising an optogenetic enzyme construct of the invention.

An inner retinal cell of the invention may be a bipolar cell or a ganglion cell. Retinal bipolar cells are second-order interneurons that rely on electrical signals between photoreceptors and ganglion cells. They act, directly or indirectly, to transmit signals from the photoreceptors to the ganglion cells. They synapse with photoreceptors and horizontal cells. The bipolar cells then transmit the signals from the photoreceptors or the horizontal cells to the ganglion cells directly or indirectly (via amacrine cells). A retinal ganglion cell (RGC) is a type of neuron located near the inner surface (the ganglion cell layer) of the retina of the eye. It receives visual information from photoreceptors via two intermediate neuron types: bipolar cells and amacrine cells. Retinal ganglion cells vary significantly in terms of their size, connections, and responses to visual stimulation but they all share the defining property of having a long axon that extends into the brain. These axons form the optic nerve, optic chiasm, and optic tract.

In yet another aspect, the present disclosure encompasses a method of restoring vision to a subject. The method comprises identifying a subject with loss of vision due to a deficit in light perception or sensitivity, administering a composition comprising a vector, the vector comprising an optogenetic red-shift construct of the invention, activating the optogenetic device with light, and measuring light sensitivity in the subject, wherein increased light sensitivity indicates vision restoration. Alternatively, the method comprises co-administering a composition comprising a first vector, the first vector comprising an optogenetic device construct of the invention and a composition comprising a second vector, the second vector comprising an optogenetic enzyme construct of the invention. It is standard in the art to determine a subject's ability to perceive light.

Methods of identifying a subject with a deficit in light perception or sensitivity are known in the art. For example, a contrast sensitivity test may be used to measure a subject's ability to distinguish between finer and finer increments of light versus dark (contrast). Devices used to test contrast sensitivity may include the Pelli Robson contrast sensitivity chart or sine-wave grating tests. Detailed contrast sensitivity measurements that include both size (spatial frequency) and contrast are used to plot a person's contrast sensitivity function (CSF). A subject's contrast sensitivity function essentially is a plotting of the curve that defines the lowest contrast level that a subject can detect for each spatial frequency tested. Additionally, optical coherence tomography (OCT) may be used to measure sensitivity to light. The foregoing methods may be used to determine if the subject experiences an increased sensitive to light following administration of a composition of the invention.

In still yet another aspect, the present disclosure encompasses a method of treating retinal degeneration. The method comprises identifying a subject with retinal degeneration due to loss of photoreceptor function, administering a composition comprising a vector, the vector comprising an optogenetic red-shift construct of the invention, activating the optogenetic device with light, and measuring light sensitivity in the subject, wherein increased sensitivity to light indicates treatment of retinal degeneration. Alternatively, the method comprises co-administering a composition comprising a first vector, the first vector comprising an optogenetic device construct of the invention and a composition comprising a second vector, the second vector comprising an optogenetic enzyme construct of the invention. Loss of photoreceptor function may be detected by a deficit in light perception or sensitivity. In a specific embodiment, the loss of photoreceptor function may be due to loss of photoreceptor cells. In another specific embodiment, the retinal degeneration may be retinitis pigmentosa.

Retinal degeneration is used to describe a wide range of retinal disorders which cause varying degrees of progressive visual dysfunction and blindness. Retinal degeneration may be caused by photoreceptor loss. Retinal degeneration may include, but is not limited to, Stargardt disease, retinitis pigmentosa, and rod-cone/cone-rod dystrophies. Methods of identifying a subject with retinal degeneration are known in the art. For example, routine clinical ocular examination, kinetic perimetry, fundus photography, dark adaptometry, multielectrode array (MEA) system and electroretinography (ERG) may be used to assess the function of the retina. ERG may include recording of focal macular ERGs or multifocal ERG (mfERG). Additionally, identifying a subject with retinal degeneration may include genetic testing to identify mutations using, for example, but not limited to, Sanger sequencing, APEX arrays, High Throughput or next-generation sequencing (NGS).

In yet still another aspect, the present disclosure encompasses a method of restoring photoreceptor function in a human eye, the method comprising administering an effective amount of a composition comprising a vector, the vector comprising an optogenetic red-shift construct of the invention. Alternatively, the method comprises co-administering a composition comprising a first vector, the first vector comprising an optogenetic device construct of the invention and a composition comprising a second vector, the second vector comprising an optogenetic enzyme construct of the invention.

In a specific embodiment, the composition may be administered via intravitreal or subretinal administration. A composition may be administered in an amount effective to restore photoreceptor function. An "effective amount" is an amount of optogenetic device sufficient to restore photoreceptor function as measurable by light sensitivity. Actual dosage levels of an optogenetic device may be varied so as to administer an amount that is effective to achieve the desired therapeutic response for a particular subject. The selected dosage level will depend upon a variety of factors which may include, but are not limited to, the AAV serotype, the promoter strength, the level of photoreceptor loss in the subject, and the physical condition and prior medical history of the subject being treated.

A method of the invention further comprises activating the optogenetic device with light. Current optogenetic strategies require high-intensity blue light to stimulate optogenetic devices posing a risk of retinal damage. According to the invention, the optogenetic device may be activated with light that is shifted toward the red end of the spectrum (i.e. has a longer wavelength) relative to the wavelength of light that the optogenetic device responds to in absence of a retinoid processing enzyme. In a specific embodiment, the opotogenetic device may be activated with red, far red, or infrared light. Methods to activate optogenetic devices with light are known in the art. For example, light may be projected onto the retina. A monochromatic light source may be used to provide light, light flashes, or periodic light pulses at defined wavelengths. Light may be applied using stimulator goggles with an adaptive front sensor array and an LED array (or other patterned light source) facing the eye. Light may be applied at a wavelength at which the optogenetic device is activated. For example, light may be applied at a wavelength greater than 495 nm, or greater than 570 nm, or greater than 590 nm, or greater than 620 nm. In an embodiment, light may be applied at a wavelength of about 495 nm to about 570 nm. In another embodiment, light may be applied at a wavelength of about 570 nm to about 590 nm. In still another embodiment, light may be applied at a wavelength of about 590 nm to about 620 nm. In yet still another embodiment, light may be applied at a wavelength of about 620 nm to about 750 nm. In a further another embodiment, light may be applied at a wavelength of about 710 nm to about 850 nm. In a different embodiment, light may be applied at a wavelength of about 700 nm to about 1050 nm. In a specific embodiment, light may be applied at a wavelength of greater than 620 nm.

In the foregoing embodiments, an eye exam may be used to detect vision loss. An eye exam may include specialized tests including, but not limited to, direct ophthalmoscopy, indirect ophthalmoscopy, applanation tonometry, corneal and retinal topography, fluorescein angiogram, dilated pupillary exam, refraction, and slit-lap exam. In an embodiment, a method of the invention may comprise identifying a subject with more than 55%, more than 60%, more than 65%, more than 70%, or more than 75% vision loss. In another embodiment, a method of the invention may comprise identifying a subject with more than 80%, more than 85%, more than 90%, or more than 95% vision loss. In another embodiment a method of the invention may comprise identifying a subject that is blind.

(c) Subject

A subject of the invention may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the subject is a mouse. In other preferred embodiments, the subject is a human.

Definitions

The term "polynucleotide" is intended to encompass a singular nucleic acid as well as plural nucleic acids, and refers to an isolated nucleic acid molecule or construct, e.g., messenger RNA (mRNA), cDNA, or vector DNA. A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a optogenetic device and/or retinoid processing enzyme contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into ammo acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an optogenetic device and a retinoid processing enzyme or a single vector may separately encode an optogenetic device and a second different optogenetic device. In addition, a vector, polynucleotide, or nucleic acid of the invention may encode heterologous coding regions, either fused or unfused to a nucleic acid encoding a an optogenetic device and/or retinoid processing enzyme. Heterologous coding regions include without limitation specialized elements or motifs, such as a signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. The term "control regions" refers to DNA sequences necessary for the expression of an operably linked coding sequence in a particular host organism. The control regions that are suitable for prokaryotes, for example, include a promoter, optionally an operator sequence, and a ribosome binding site. Eukaryotic cells are known to utilize promoters, polyadenylation signals, and enhancers. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an optogenetic device signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

A "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

"Isolated," when used to describe the various polypeptides disclosed herein, means a polypeptide has been identified and separated and/or recovered from a cell or cell culture from which it was expressed. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

An "isolated" nucleic acid encoding a polypeptide or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

An "isolated" cell is a cell isolated from a native source.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction for Examples 1-3

Significant technological challenges in the field of optogenetics remain. One problem, is that light penetrates brain tissue rather poorly. All tissues scatter light, with the extent of scattering decreasing with increasing wavelength[3]. An additional barrier to light penetration into brain is the presence of hemoglobin in blood which strongly absorbs light in the 500-600 nm range[3]. Since hemoglobin's absorption drops off rapidly beyond 600 nm, designing optogenetic tools that can operate in the far red or infrared region is a highly desirable goal[1]. In addition, if optogenetic tools are ever to be used therapeutically, the size of the human brain will necessitate the development of devices that can be controlled at a considerable distance from the light source. Since the majority of optogenetic actuators operate in the 450-600 nm range[1,2], scattering and absorption remain significant barriers to realizing the full potential of optogenetics.

A second barrier to progress in optogenetics is that the action spectra of many commonly used optogenetic actuators overlap extensively with the excitation spectra of optogenetic sensors (e.g., genetically encoded fluorescent voltage or calcium indicators)[1,4]. This overlap is often so extensive that it is impossible to independently image the sensor without activating the actuator[1]. Thus, the combined use of optogenetic actuators and sensors, though highly desirable, has only been achieved in a handful of cases[7,12]. In addition, spectral overlap between actuators poses a significant barrier to implementing independent optogenetic control of two different neuronal sub-populations in the same region of the brain, another sought-after goal[1,7]. Clearly, the problem of spectral overlap remains a significant hurdle in the field of optogenetics.

In order to address the spectral overlap problem, there has been a major push to develop red-shifted actuators and sensors[4-7,12]. Some groups have used bioprospecting to identify actuators with red-shifted excitation spectra[4,5], whereas others have employed protein engineering to generate red-shifted variants of existing actuators or sensors[6,7,12]. For example, in a recent study, a red-shifted channelrhodopsin with an excitation maximum of 545 nm (C1V1-ET) was engineered, via a combination of domain-swapping between two different channelrhodopsins and amino acids substitutions in the chromophore-binding cleft[6]. However, the authors reported in their Discussion that attempts to further red-shift the C1V1-ET variant beyond 545 nm were unsuccessful[6]. It therefore appears that there are limits to the extent of red-shift achievable by rational protein engineering alone. Clearly, we need new, orthogonal approaches to the problem of red-shifting optogenetic actuators.

The goal of the present invention is to introduce a novel biomimetic strategy for red-shifting optogenetic actuators: red-shifted chromophore substitution. This approach is complementary to protein engineering and is based on a strategy used by migrating fish to enable better vision in turbid water. Migratory fish species such as salmon spend a portion of their lives in the open ocean, where the spectral distribution of light is centered around 480 nm[8]. When these fish migrate into inland streams to spawn, they reprogram their photoreceptors to adapt to the red-shifted spectrum of light in the turbid inland waters[8,9]. This reprogramming includes two components: a replacement of some opsin proteins with red-shifted variants, and the expression of an unidentified enzyme (referred to here as 'enzyme X', later discovered to be Cyp27c1) that introduces a double bond into the terminal β-ionone ring of the visual chromophore, retinal, to create 3,4-dehydroretinal (FIG. 1A)[8,9]. The replacement of retinal by 3,4-dehydroretinal in the opsin protein causes a red-shift of the opsin's action spectrum on account of the additional conjugated double bond in 3,4-dehydroretinal (arrow in FIG. 1A)[8,9]. The combined effect of opsin protein replacement and formation of 3,4-dehydroretinal is to red-shift the fish's visual sensitivity to match that of the red-shifted milieu of their new freshwater environment[8,9]. For example, coho salmon (*Oncorhynchus kisutch*) achieve a total red-shift of 53 nm in their green cone action spectrum upon migration[9]. This shift results from the combined expression of a green cone opsin isoform that is red-shifted by 17 nm (due to a Q122E substitution in the chromophore binding cleft) plus the formation of 3,4-dehydroretinal by enzyme X (Cyp27c1) which effects an additional shift of 36 nm. In this case, chromophore substitution accounts for more than two-thirds of the total red-shift. Thus, migratory fish have evolved a remarkable dual strategy for red-shifting their opsins which includes both protein 'engineering' and chromophore substitution.

Our invention involves a similar dual strategy for optogenetics. Up to now, efforts to red-shift optogenetic actuators have focused exclusively on the protein and not on the chromophore. Our goal is to introduce red-shifted chromophore substitution as a complementary strategy to protein engineering. A key feature of this approach is that chromophore substitution can be paired with any existing optogenetic actuator. This invention will have a major impact on a wide range of basic and clinical applications in optogenetics. First, it will permit better spectral separation between optogenetic actuators and sensors, thereby enabling neuroscientists to couple the use of optical control and readout in a single experiment. Second, it will facilitate the combined use of two actuators within distinct neuronal sub-populations, thus allowing more sophisticated analyses of neural circuit function. Lastly, it will permit some optogenetic actuators to operate beyond 650 nm, well outside of the hemoglobin absorption window. This last feature will permit optogenetic control of neurons deeper in the brain, and will be of benefit in clinical applications in large-brained humans. Interestingly, data from vertebrate opsins suggest that the longer the wavelength of the sensitivity peak of the retinal-based opsin, the greater the red-shift upon substitution of 3,4-dehydroretinal[13]. Thus, as further red-shifted optogenetic actuators are identified by bioprospecting, chromophore substitution holds the promise of ever greater shifts toward the near-infrared.

Example 1. Identification of the Enzyme Mediating the Conversion of Retinal Into 3,4-dehydroretinal—Cyp27c1

Figure 12:
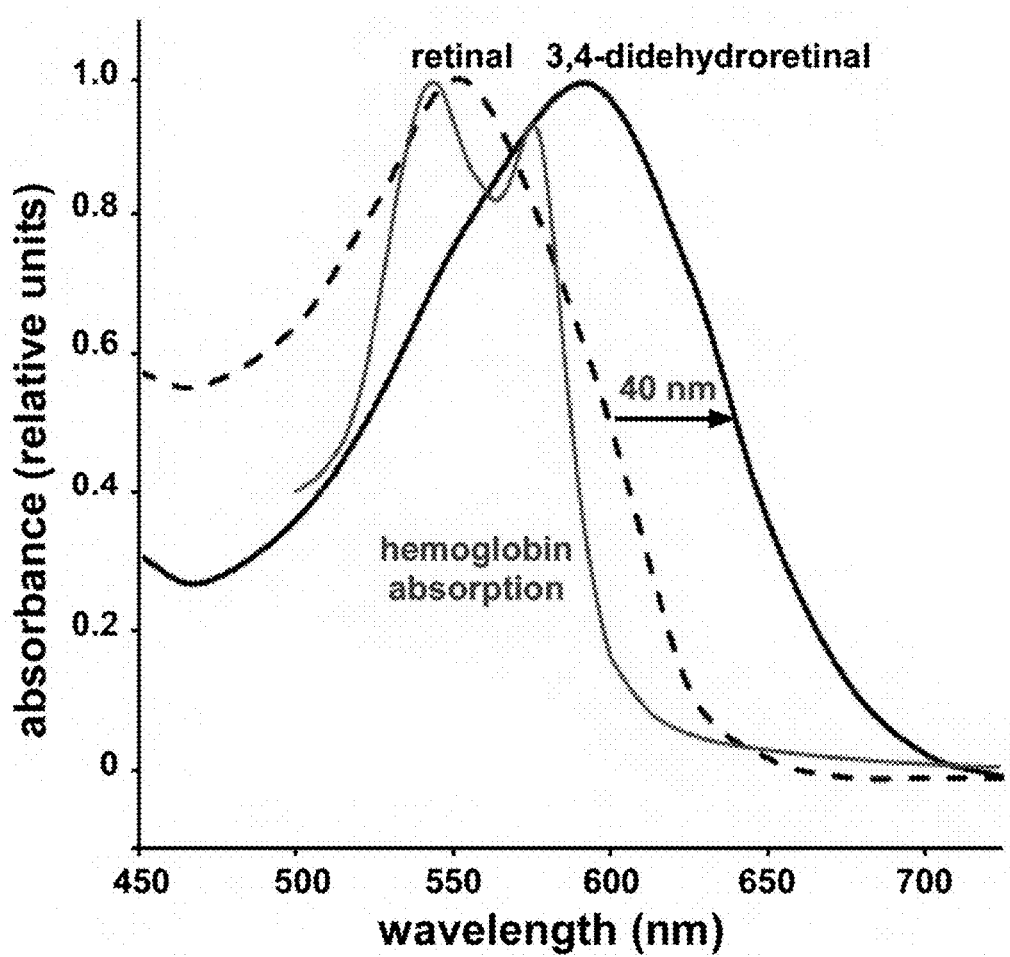
FIG. 12 depicts a graph (adapted from *Biochemistry* 51: 4499-506) demonstrating the red-shift induced by substituting 3,4-didehydroretinal (solid black curve) in place of retinal (dotted black curve) in the archaerhodopsin proton pump, AR-3, expressed in *E. coli*. Note that the wavelength of half-maximal absorption on the red slope of the curve is red-shifted 40 nm (from 599 to 639 nm), permitting control of the optogenetic device with light beyond 650 nm. This shift largely relieves the spectral overlap with hemoglobin (red curve).

Optogenetic actuators utilize all-trans retinal (henceforth 'retinal') as their chromophore[2]. The fortuitous presence of retinal in mammalian neurons enables the use of these actuators in vivo. In a recent study, Spudich and colleagues showed that replacement of retinal with 3,4-dehydroretinal in optogenetic actuators in vitro can red-shift their action spectra (FIG. 12)[10]. Unfortunately, the mammalian brain neither accumulates nor synthesizes 3,4-dehydroretinal, thus it is currently impossible to implement red-shifted chromophore substitution in vivo. The goal of this Example is to employ a biomimetic strategy to solve this problem. Migratory fish achieve a remarkable red-shift in their spectral sensitivity by inducing the expression of an enzyme that converts retinal into 3,4-dehydroretinal[9]. In this Example, we will utilize expression profiling in zebrafish to identify this enzyme.

It was recently shown that the physiological transformation that salmon undergo upon migration can be mimicked by treating zebrafish with thyroid hormone[14]. After three weeks of exposure to thyroid hormone, zebrafish opsins undergo a red-shift in their spectral sensitivity as demonstrated by microspectrophotometry of photoreceptor outer segments[14]. We treated zebrafish with thyroid hormone for three weeks, and then assayed the retinoid content of their retinas by HPLC (high performance liquid chromatography). We found a quantitative conversion of retinal into 3,4-dehydroretinal in the retinas of thyroid hormone-treated zebrafish (FIG. 1E-H).

Figure 2A:
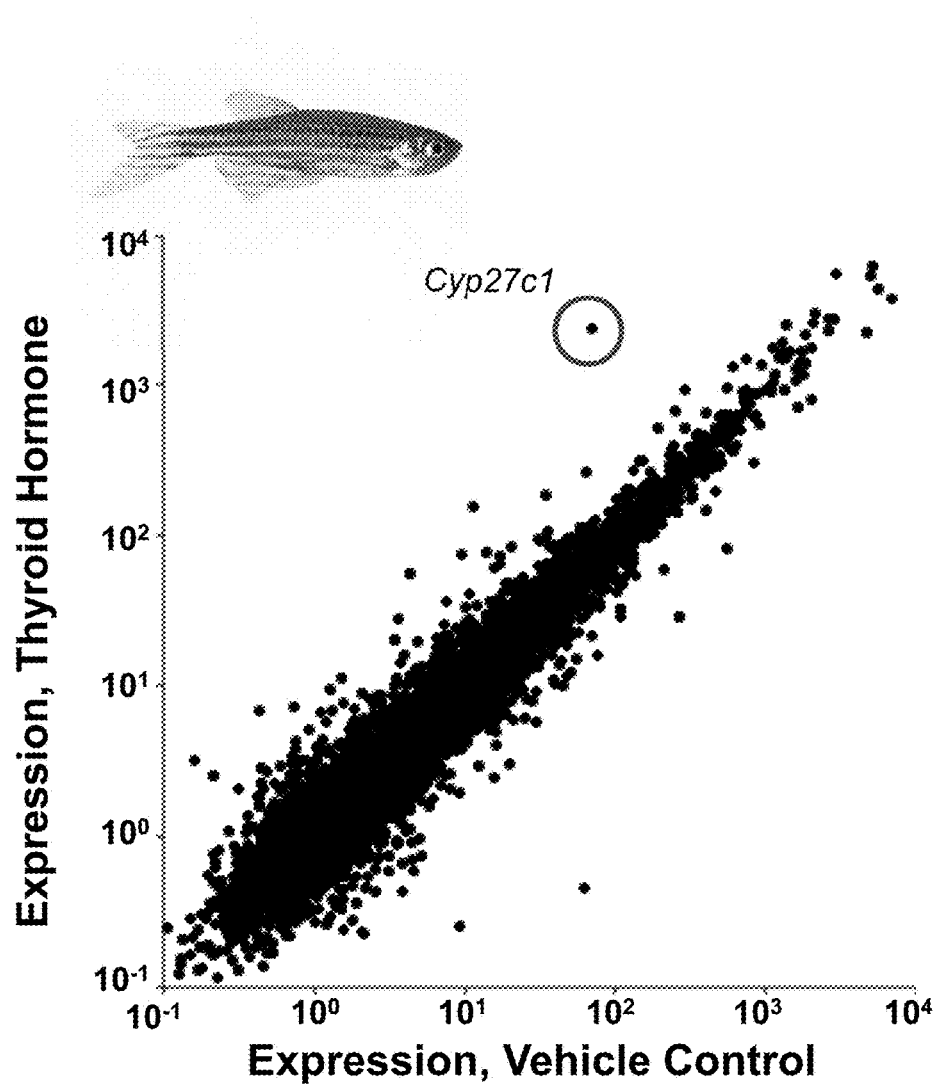
FIG. 2A and FIG. 2B depict the results of RNA-seq-based expression profiling of zebrafish and bullfrog retinal pigment epithelium (RPE).
Figure 7:
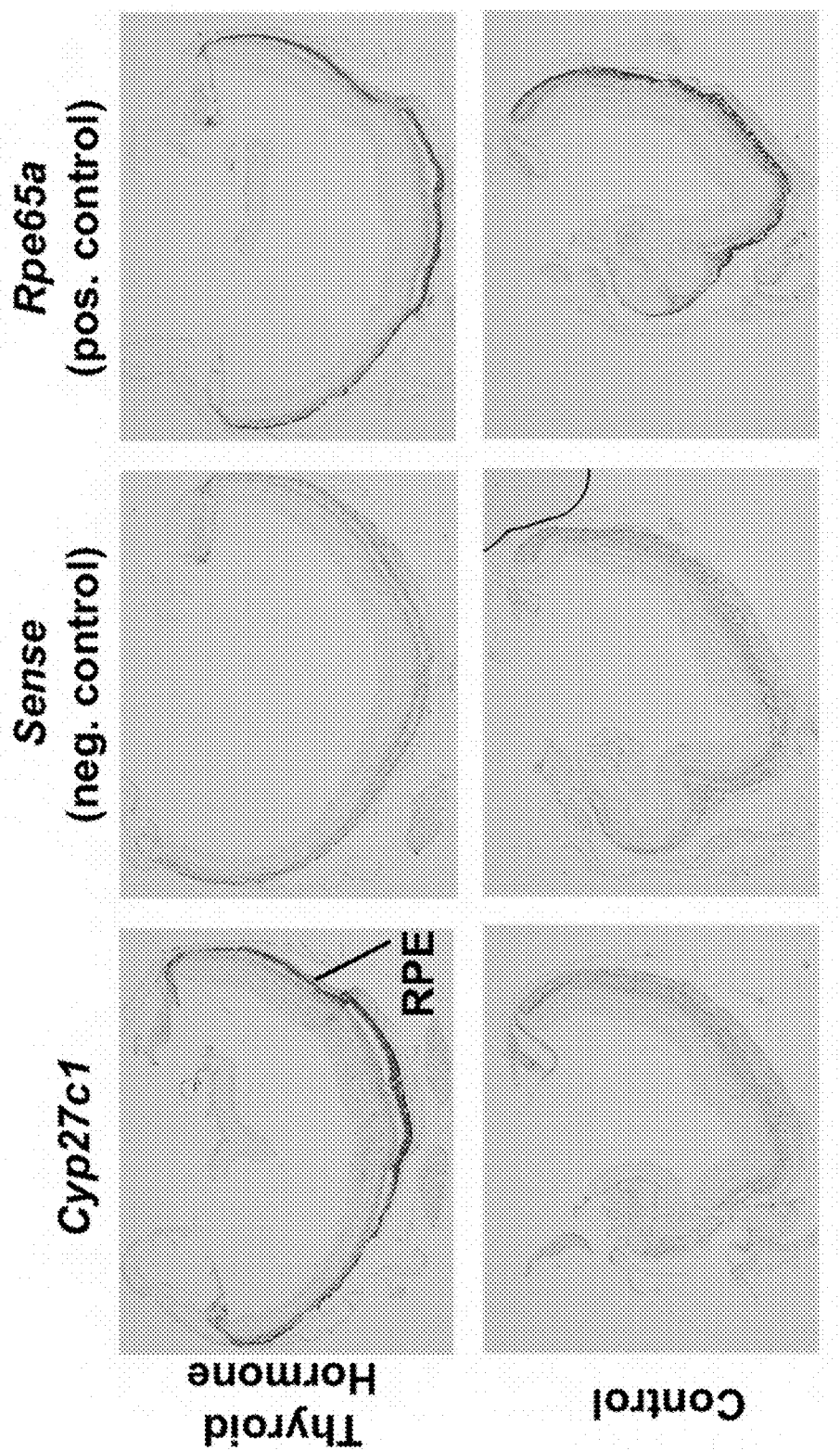
FIG. 7 depicts images that show that the cyp27c1 transcript is enriched in the RPE of thyroid-hormone treated zebrafish, but not in untreated controls.
Figure 8:
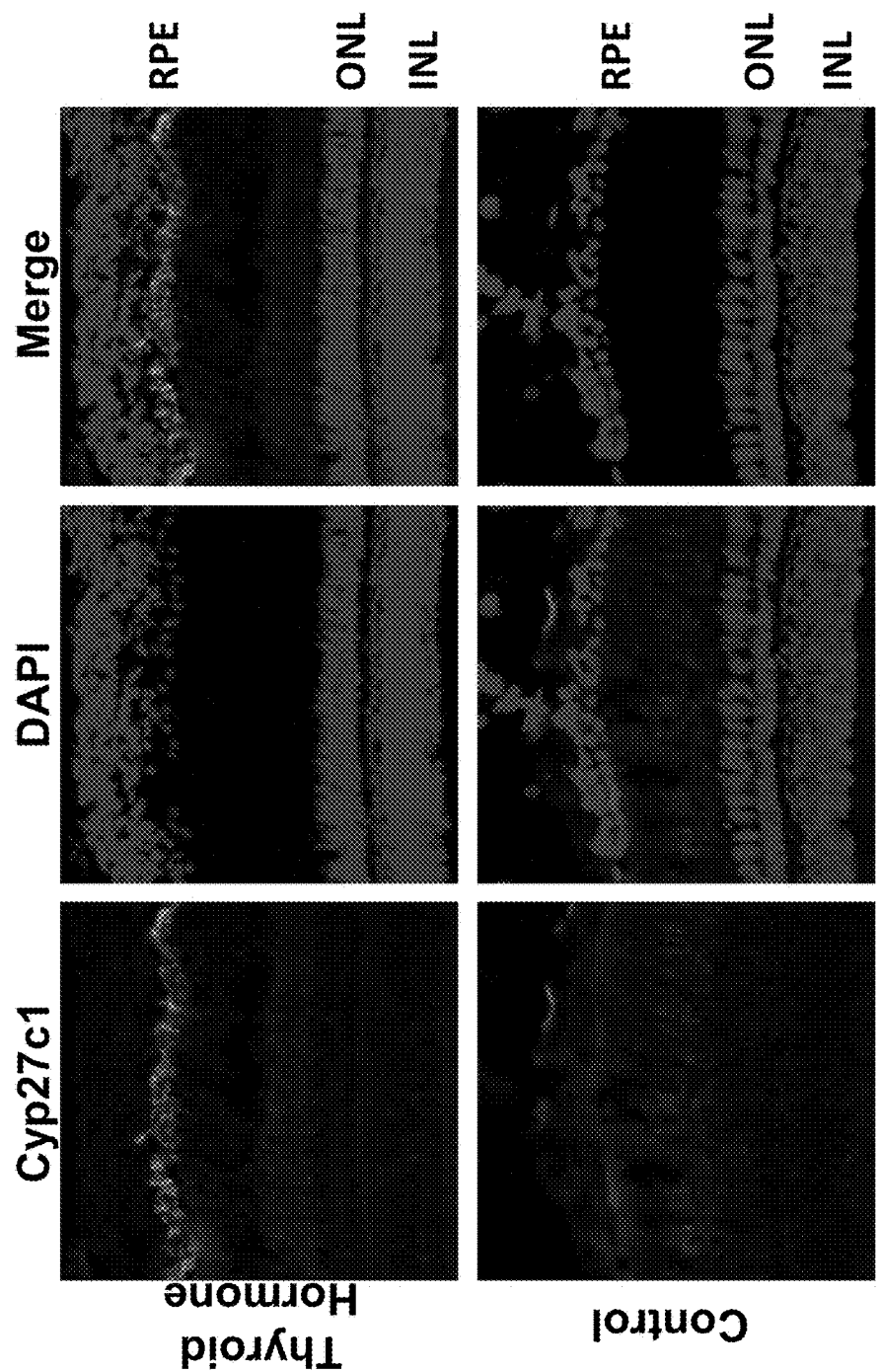
FIG. 8 depicts images that show that Cyp27c1 protein is enriched in the RPE of thyroid-hormone treated zebrafish, but not in untreated controls.

It has long been postulated that the conversion of retinal into 3,4-dehydroretinal in migratory fish is mediated by a 'terminal ring dehydrogenase'[8]. We postulated that the expression of this enzyme is strongly induced in thyroid hormone-treated zebrafish. To identify the transcript encoding this enzyme, we carried out transcriptome profiling of thyroid hormone-treated fish and compared them to vehicle-treated controls. We hypothesized that the enzyme was likely to be expressed in one of three tissues: retinal pigment epithelium (which lies immediately adjacent to photoreceptors and is a known source of retinoids), retina or liver. We obtained RNA-seq data for RPE and identified an excellent candidate transcript, flj13639. This transcript encodes an 'orphan' member of the cytochrome P450 family of monooxygenases, Cyp27c1 (FIG. 2A). Since many cytochrome P450 family members are known to mediate metabolic transformation of small molecules[52,53], Cyp27c1 represented an attractive candidate for the enzyme we were seeking. Analysis of the RPE in thyroid-hormone treated zebrafish showed that cyp27c1 transcript is enriched in the RPE (FIG. 7) and that Cyp27c1 protein is enriched in the RPE (FIG. 8). Accordingly, this data supported our belief that Cyp27c1 is the sought after enzyme.

Figure 1I:
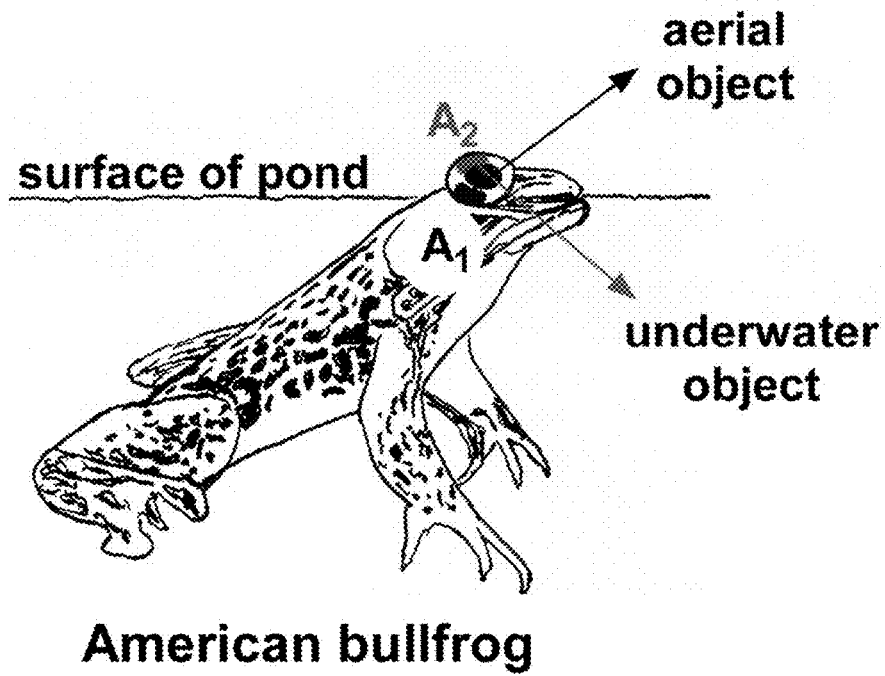
Figure 1J:
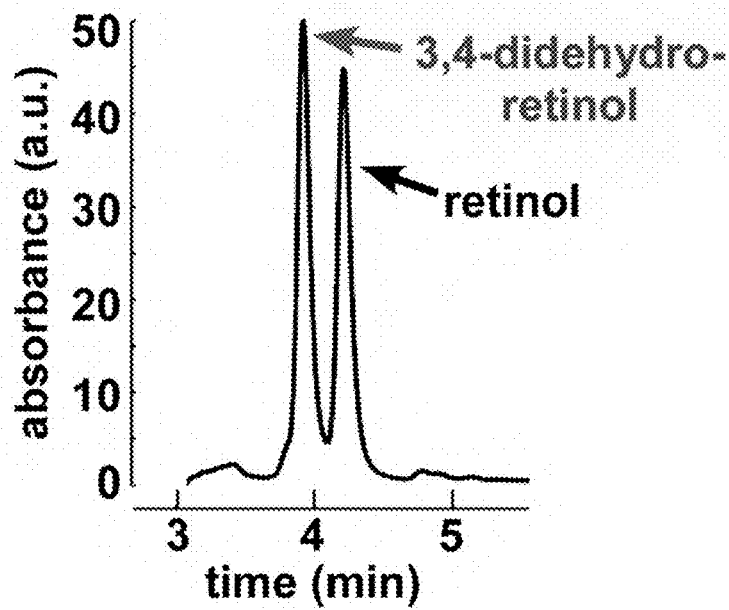
Figure 1K:
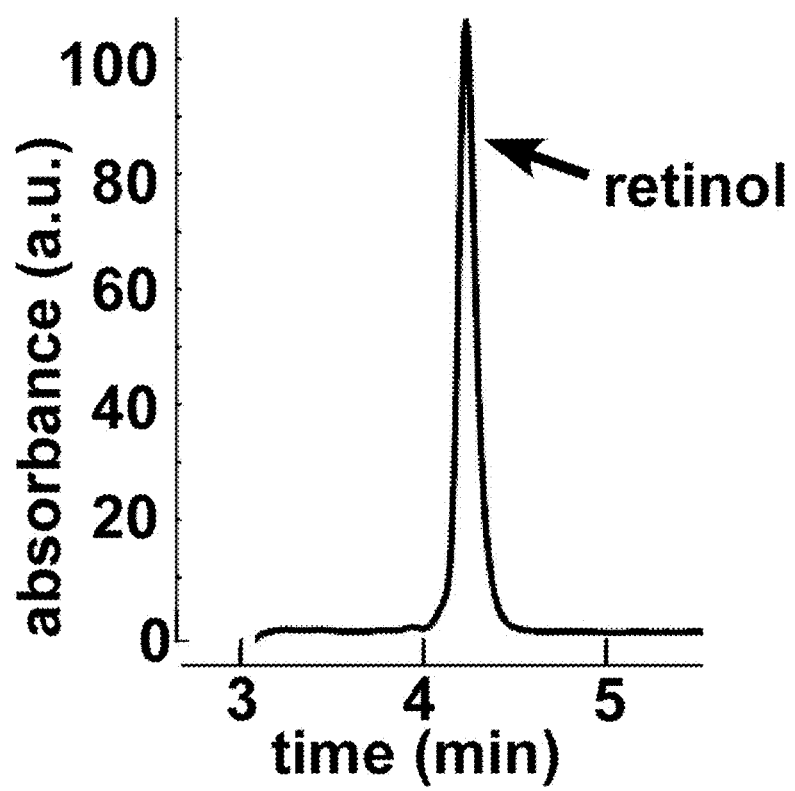
Figure 2B:
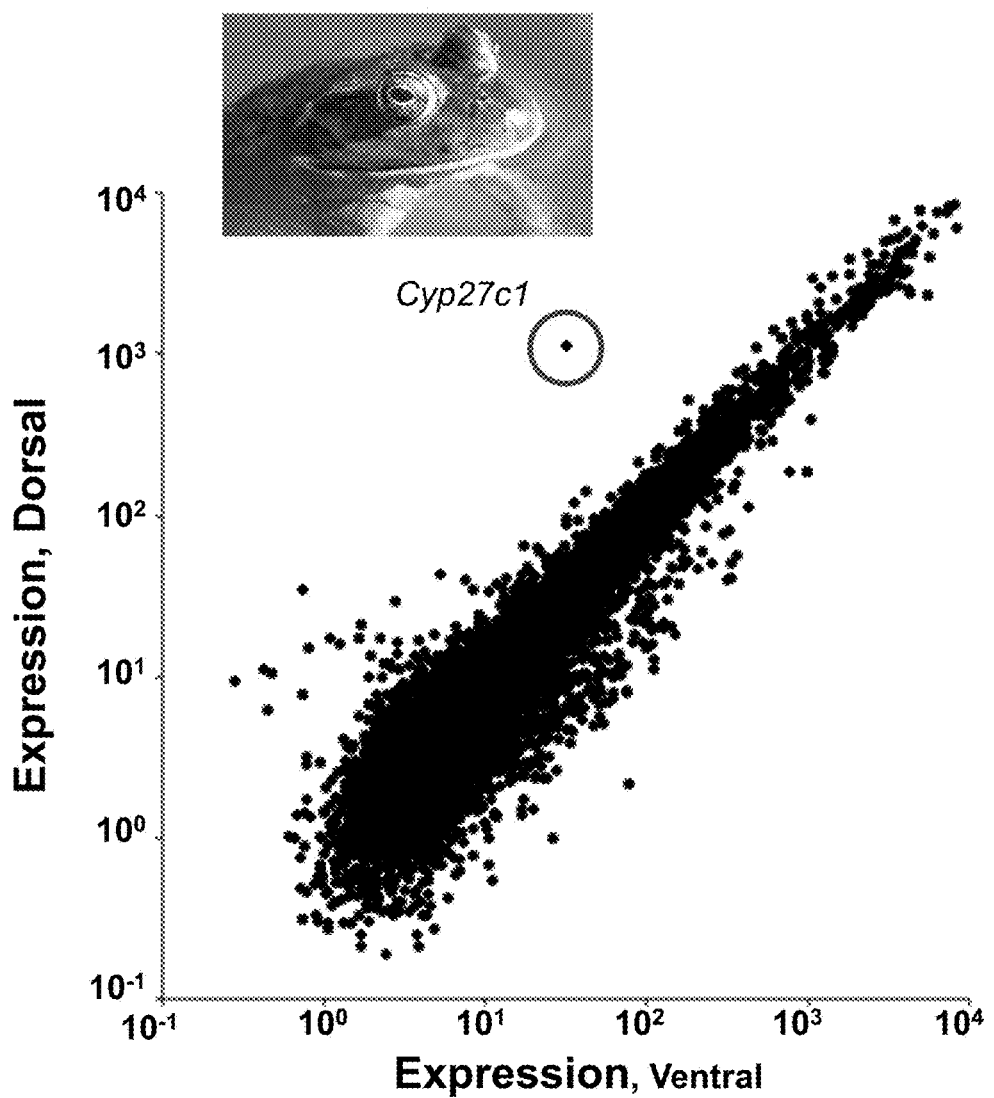
Figure 4A:
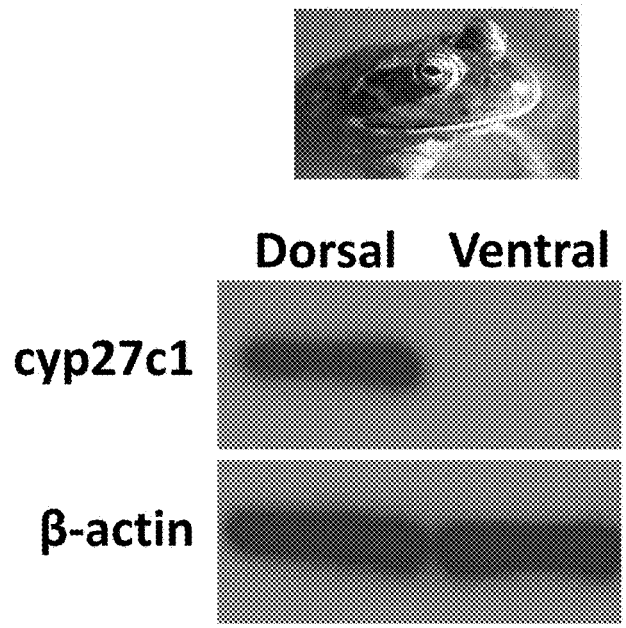
FIG. 4A and FIG. 4B depict Western blots showing that Cyp27c1 protein is enriched in bullfrog and zebrafish.
Figure 4B:
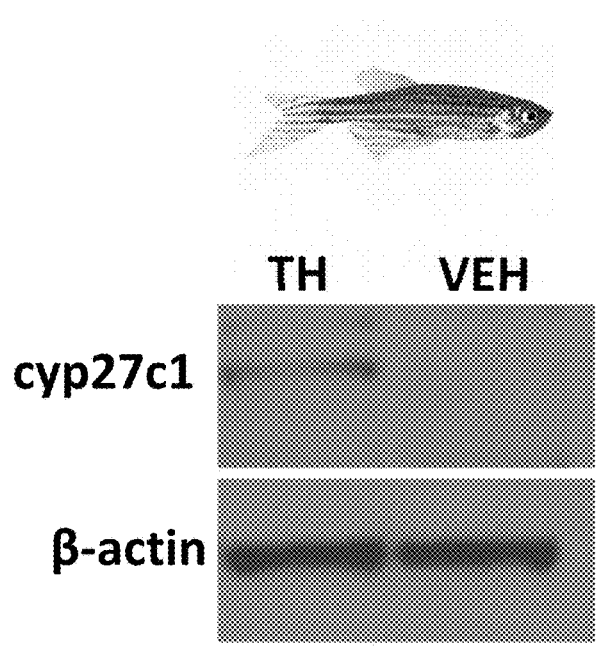
Figure 5A:
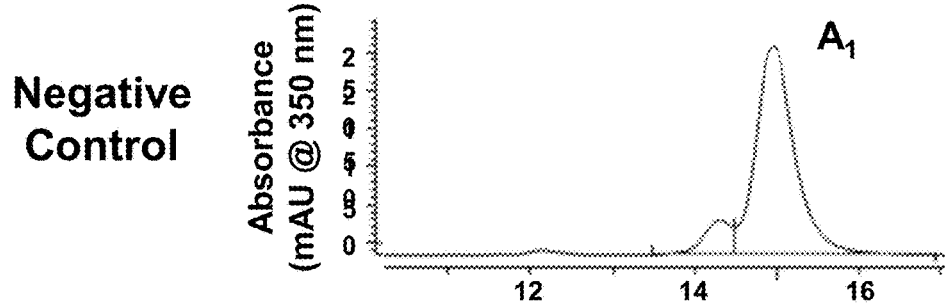
FIG. 5A, FIG. 5B, FIG. 5C, FIG. 5D and FIG. 5E depict the results of introducing an expression construct containing the zebrafish ortholog of Cyp27c1 into HEK293 cells and incubating with retinol for 24 hours (vitamin $A_1$).
Figure 5B:
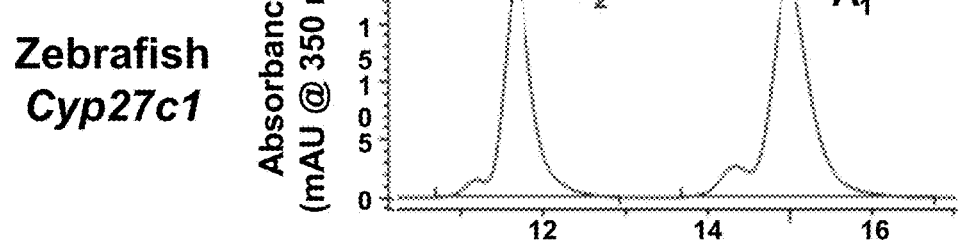
Figure 5C:
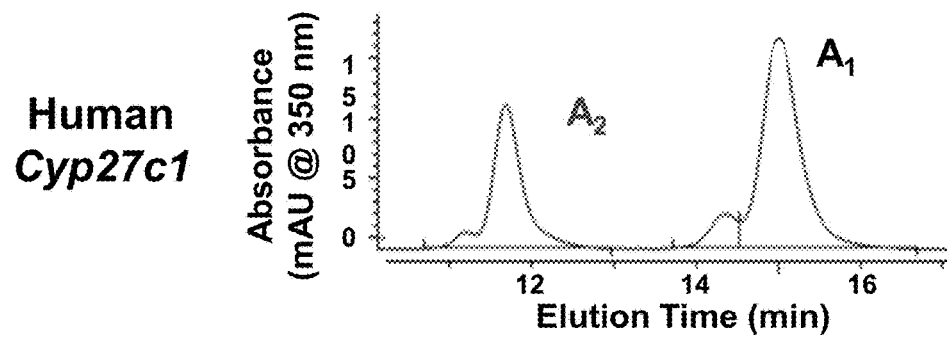
Figure 5D:
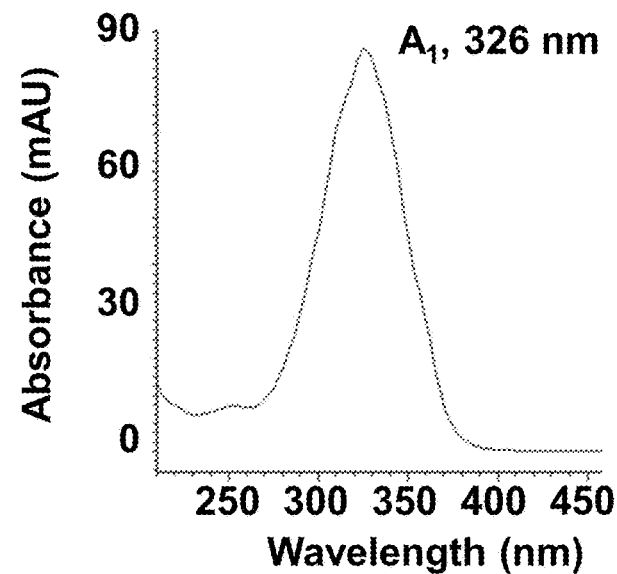
Figure 5E:
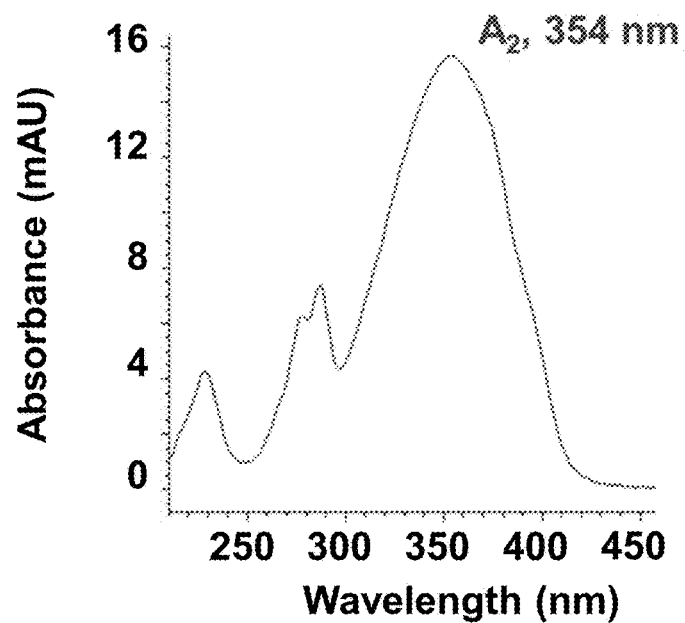

In parallel studies, we exploited a unique feature of the bullfrog (*Lithobates catesbeianus*) retina to identify candidate genes. In 1971, George Wald and colleagues reported that the dorsal, but not the ventral, retina of adult bullfrogs contains 3,4-didehydroretinal, which is thought to facilitate downward vision into murky, red-shifted pond water[18]. To confirm this result, we analyzed dorsal and ventral bullfrog retina and RPE by HPLC, RNA-seq and Western blot. We found 3,4-didehydroretinal in dorsal, but not ventral, retina (FIGS. 1I-K) and a corresponding high-level enrichment for a single gene in dorsal RPE: Cyp27c1 (FIG. 2B). Further, Western blot analysis of Cyp27c1 in the dorsal versus ventral retina of bullfrogs and thyroid-treated versus untreated zebrafish revealed that Cyp27c1 is enriched in the dorsal retina of bullfrogs and the thyroid-treated zebrafish (FIG. 4A,B). The differential expression of the same enzyme in the RPE of two species separated by >400 million years of evolution gave us confidence that Cyp27c1 represented the long-sought retinal 3,4-dehydrogenase.

Figure 3:
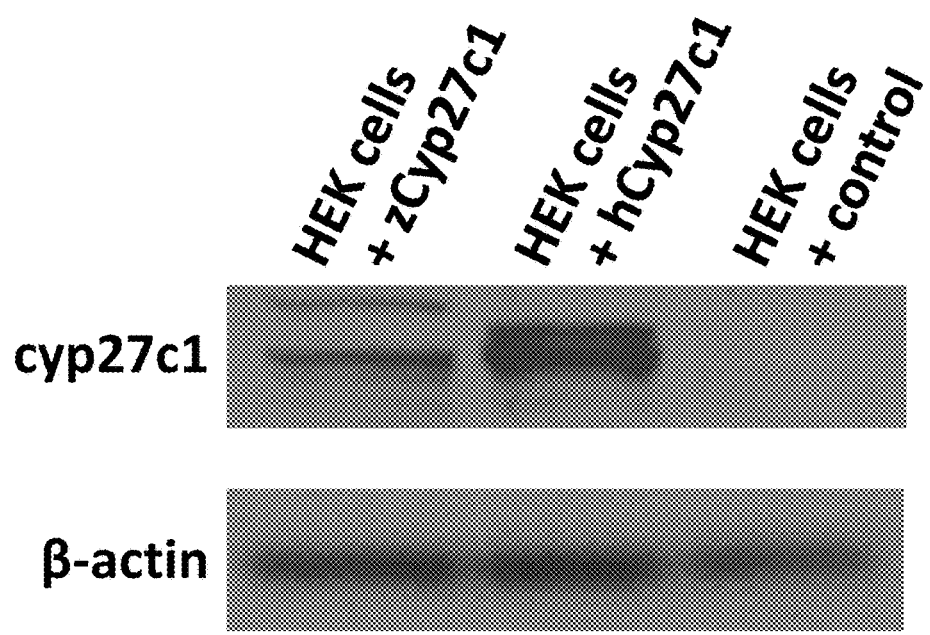
FIG. 3 depicts a Western blot showing that an anti-Cyp27c1 antibody successfully labels Cyp27c1 expressed in HEK-293 cells. Both zebrafish and human Cyp27c1 expressed in HEK cells are readily detected with the anti-Cyp27c1 antibody.

Next, we determined if Cyp27c1 is sufficient to convert retinal to 3,4-didehydroretinal. We cloned a full-length zebrafish Cyp27c1 cDNA and a full-length human Cyp27c1 cDNA into a mammalian expression vector and expressed it in HEK293 cells. FIG. 3 confirms that the recombinant zebrafish and human Cyp27c1 are expressed in the HEK293 cells. After 24 hours of incubation with retinol ($A_1$), HPLC showed accumulation of significant quantities of 3,4-didehydroretinol ($A_2$) (the alcohol form of 3,4-didehydroretinal) in the Cyp27c1-transfected cells but not in cells transfected with an empty vector (FIG. 5). This result confirmed that Cyp27c1 is 'enzyme X'.

Figure 6:
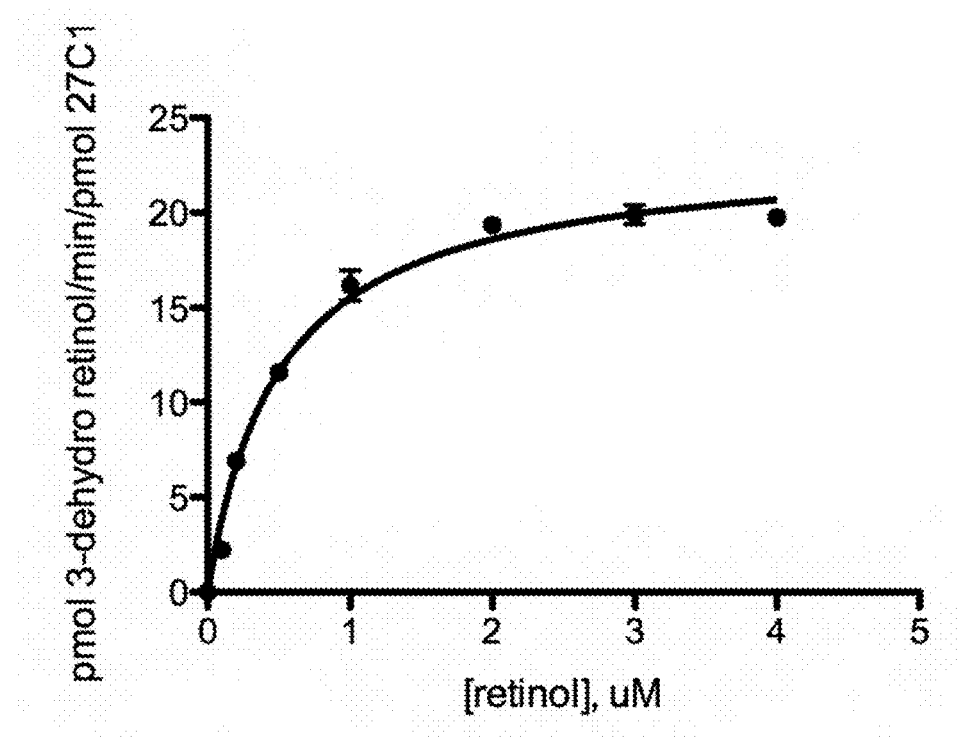
FIG. 6 depicts a Michaelis-Menten curve for the activity of zebrafish Cyp27c1 in converting retinol into 3,4-didehydroretinol.

Isolated Cyp27c1 was used to determine its enzymatic activity. FIG. 6 demonstrates a Michaelis-Menten curve for the activity of zebrafish Cyp27c1 in converting retinol to 3,4-didehydroretinol. This data confirms that we have identified the enzyme responsible for the retinol conversion.

Figure 10A:
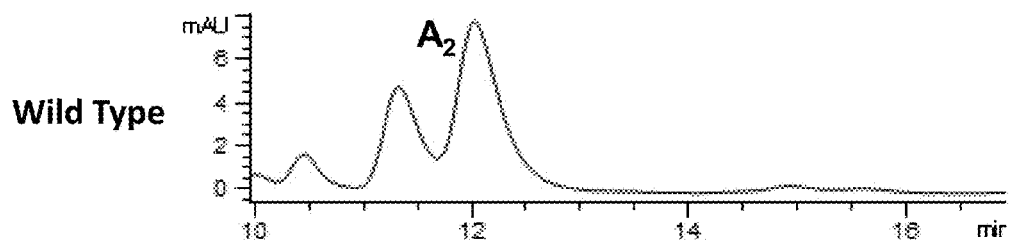
FIG. 10A, FIG. 10B, FIG. 10C and FIG. 10D depict graphs showing that Cyp27c1 mutant zebrafish do not make vitamin $A_2$ after thyroid hormone treatment.
Figure 10B:
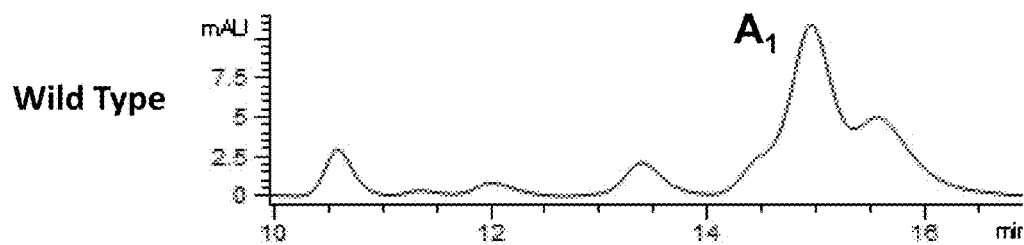
Figure 10C:
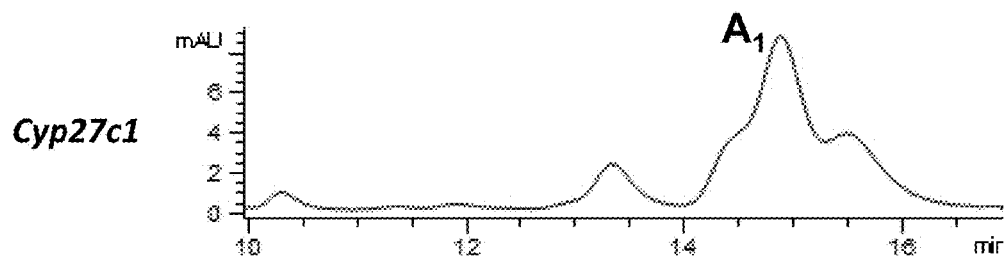
Figure 10D:
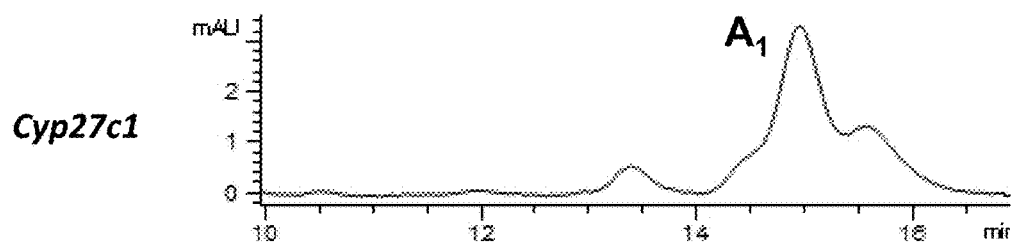

To continue to probe the effects of Cyp27c1, we generated cyp27c1 null mutant zebrafish. FIG. 9 shows that in the thyroid hormone-treated cyp27c1 null mutant zebrafish, Cyp27c1 cannot be identified in the RPE. We then utilized the mutant zebrafish to identify their ability to covert retinol ($A_1$) to 3,4-didehydroretinol ($A_2$). FIG. 10 shows that in the thyroid hormone-treated zebrafish, wild-type zebrafish had sufficient quantities of $A_2$ (FIG. 10A), whereas the cyp27c1 null mutant zebrafish were unable to convert $A_1$ to $A_2$ and only had sufficient quantities of $A_1$ (FIG. 10C). Suction electrode recordings of red single cones from wild-type and cyp27c1 mutant fish were performed. FIG. 11 shows that cyp27c1 null mutant zebrafish fail to red-shift their photoreceptors in response to thyroid hormone treatment (FIG. 11B). Accordingly, we have convincingly demonstrated that Cyp27c1 is the enzyme responsible for conversion of Vitamin $A_1$ to Vitamin $A_2$ and this conversion results in a red-shifted sensitivity to light.

A second notable upregulated transcript from the transcriptome profiling was Opn1mw4 (4-fold upregulated), which encodes one of four green cone opsins in zebrafish[16]. Since opsins are expressed in photoreceptors and not RPE, this result indicated that there was trace photoreceptor contamination in our RPE samples. We therefore analyzed a range of photoreceptor gene transcripts in our thyroid hormone-treated 'RPE' and controls, and found similar levels of photoreceptor contamination between the two samples. Opn1mw4 was the only photoreceptor transcript that was significantly upregulated by thyroid hormone treatment. This result was notable because Opn1mw4 encodes a red-shifted variant of green cone opsin containing the same Q122E cleft as the one found in the green cone opsin isoform induced in coho salmon cones upon migration[9,16]. This result suggested that thyroid treatment of zebrafish induces a reprogramming of both RPE and photoreceptors very similar to that which occurs in migrating fish.

Example 2. Utilization of Red-Shifted Chromophore Substitution to Control Neuronal Activity Deep within Brain Tissue Poor light penetration makes it difficult to utilize optogenetic actuators deep in the brain[1]. In this Example, we will utilize multielectrode array (MEA) recordings of neurons in explanted mouse vomeronasal organ (VNO) to determine whether co-expression of Cyp27c1 with an optogenetic actuator can extend the tissue depth at which the actuator can function.

The irregular morphology of the intact mouse brain makes it a difficult system in which to rigorously measure the tissue depth at which an optogenetic actuator can function. Accordingly, we have chosen to establish an ex vivo system in which to test the hypothesis that co-expression of an actuator and Cyp27c1 will extend the tissue depth at which the actuator can operate. We will utilize MEA recordings of explanted mouse VNO for this purpose[19].

The VNO is the primary sensory organ of the accessory olfactory system and mediates pheromone detection[19]. We will explant the VNO on top of a MEA and maintain it in a perfusion chamber topped by a glass coverslip that is covered with an opaque coating except for a 2 mm-diameter hole immediately overlying the explanted organ. The VNO explants will derive from two different transgenic mouse lines carrying expression constructs knocked into the same genomic locus (to control for variation in transgene expression). The experimental mice will carry a transgene expressing a red-shifted channelrhodopsin[6] (C1V1-ET; λmax=545 nm) along with the coding sequence for Cyp27c1 driven by the Omp promoter. Both coding sequences will be connected by a short sequence encoding the 2A peptide and thus will initially be translated as a single polypeptide and then cleaved apart at the peptide[20]. The control mice will carry an identical transgene except that the gene encoding Cyp27c1 will carry an inactivating mutation. Next, we will place a stack of 100 to 500 micron-thick coronal vibratome sections of living mouse brain on top of the coverslip overlying the VNO. The optogenetic actuator will be excited by a light source positioned above the stack of brain sections. By altering the thickness of the stack, as well as the wavelength and intensity of the light source, while recording the activity of the VNO neurons via the MEA, we will systematically measure the activity of the actuator with and without expression of Cyp27c1 as a function of tissue depth. In this way, it should be possible to determine the extent to which co-expression of Cyp27c1 extends the operational light sensitivity of the actuator.

The proposed experiment is meant to serve as a proof-of-concept that co-expression of Cyp27c1 can extend the tissue depth at which an optogenetic actuator can function. A prior study calculated that at a tissue depth of one centimeter, the 3,4-dehydroretinal-bound form of channelrhodopsin MvChR1 would be expected to absorb 13-fold more photons than the retinal-bound form[10]. Thus, in principle, red-shifted chromophore substitution has the potential to markedly extend the tissue depth of actuator function. This Example will have important implications for the eventual clinical use of optogenetic actuators in the much larger human brain, where limited tissue penetration is likely to be a significant barrier to successful implementation.

Example 3. Restoration of Color Vision to Blind Mice By Expressing an Optogenetic Actuator with and without Red-Shifted Chromophore Substitution Restoration of vision in blind patients is likely to be one of the first clinical applications of optogenetics[21]. Color vision requires comparison between two photoreceptors with spectrally distinct sensitivities. In this Example, we will restore color vision to blind mice by endowing their non-functioning cones with two different spectral sensitivities via expression of an optogenetic actuator with and without Cyp27c1.

The feasibility of restoring monochromatic vision to blind mice by optogenetics has already been demonstrated[21]. In this Example, we will restore color vision to Gnat1$^{-/-}$; Gnat2$^{-/-}$ mice that have morphologically intact, but non-functional photoreceptors. We will engineer two adeno-associated viruses (AAV): the first containing the blue cone opsin promoter driving expression of the eNpHR3.0 actuator alone (Amax=590 nm)[21], and the second containing the red cone opsin promoter driving expression of eNpHR3.0 plus Cyp27c1 (predicted Amax>620 nm). Adult blind mice will be treated by sub-retinal injection of equimolar amounts of the two viruses, and their visual performance will be evaluated six weeks later by a variety of electrophysiological and behavioral tests. In particular, color vision will be assessed by testing the mice in a behavioral three-alternative forced-choice discrimination task similar to one used previously to evaluate color vision in mice[22].

The experiment is intended to demonstrate the feasibility of achieving behaviorally-relevant channel separation between two actuators via red-shifted chromophore substitution alone. We predict that co-expression of Cyp27c1 with eNpHR3.0 will produce a red-shift of at least 30 nm (e.g., FIG. 12)[10]. Since human red-green color vision is mediated by two opsins separated by only 30 nm, the shift induced by chromophore substitution should be sufficient to support color vision. The two constructs with and without Cyp27c1 will be expressed in blue and red cones, respectively. Thus, they will be coupled to the appropriate downstream retinal circuitry for color-opponent signal processing.

This proof-of-concept experiment will demonstrate the utility of red-shifted chromophore substitution in a clinically relevant setting. Future work will expand the range of applications for red-shifted chromophore substitution and will include experiments involving the simultaneous use of actuators and sensors. A key feature of our approach is that chromophore substitution can be coupled to the use of any existing actuator in any part of the mammalian CNS. Thus, this strategy has the potential to impact almost any experiment involving optogenetics.

Red-shifted chromophore substitution is a unique and unconventional strategy for improving the utility and applicability of optogenetic devices. Given the emerging importance of optogenetics across many areas of neuroscience and the pressing need for optogenetic actuators with red-shifted spectral properties and better tissue penetration, this invention promises to have an unusually widespread impact on the field.

References for Examples 1-3

1. Alford, S. C., Wu, J., Zhao, Y., Campbell, R. E. & Knopfel, T. Optogenetic reporters. *Biol Cell* 105, 14-29 (2013).
2. Zhang, F. et al. The microbial opsin family of optogenetic tools. *Cell* 147, 1446-57 (2011).
3. Mobley, J.a.V.-D., T. Optical properties of tissues. in *Biomedical Photonics Handbook* 1-72 (CRC Press: Boca Raton, Fla., 2003).
4. Zhang, F. et al. Red-shifted optogenetic excitation: a tool for fast neural control derived from Volvox carteri. *Nat Neurosci* 11, 631-3 (2008).
5. Govorunova, E. G., Spudich, E. N., Lane, C. E., Sineshchekov, O. A. & Spudich, J. L. New channelrhodopsin with a red-shifted spectrum and rapid kinetics from Mesostigma viride. *MBio* 2, e00115-11 (2011).
6. Prigge, M. et al. Color-tuned channelrhodopsins for multiwavelength optogenetics. *J Biol Chem* 287, 31804-12 (2012).
7. Yizhar, O. et al. Neocortical excitation/inhibition balance in information processing and social dysfunction. *Nature* 477, 171-8 (2011).
8. Bridges, C. D. B. The rhodopsin-porphyropsin visual system. in *Handbook of Sensory Physiology VII/1* (ed. Dartnall, H. H. A.) 417-480 (Springer-Verlag, 1972).
9. Temple, S. E. et al. Seasonal cycle in vitamin A1/A2-based visual pigment composition during the life history of coho salmon (*Oncorhynchus kisutch*). *J Comp Physiol A Neuroethol Sens Neural Behav Physiol* 192, 301-13 (2006).
10. Sineshchekov, O. A., Govorunova, E. G., Wang, J. & Spudich, J. L. Enhancement of the long-wavelength sensitivity of optogenetic microbial rhodopsins by 3,4-dehydroretinal. *Biochemistry* 51, 4499-506 (2012).
11. Crick, F. The impact of molecular biology on neuroscience. *Philos Trans R Soc Lond B Biol Sci* 354, 2021-5 (1999).
12. Akerboom, J. et al. Genetically encoded calcium indicators for multi-color neural activity imaging and combination with optogenetics. *Front Mol Neurosci* 6, 2 (2013).

13. Harosi, F. I. An analysis of two spectral properties of vertebrate visual pigments. *Vision Res* 34, 1359-67 (1994).
14. Allison, W. T., Haimberger, T. J., Hawryshyn, C. W. & Temple, S. E. Visual pigment composition in zebrafish: Evidence for a rhodopsin-porphyropsin interchange system. *Vis Neurosci* 21, 945-52 (2004).
15. Kavanagh, K. L. et al. The SDR superfamily: functional and structural diversity within a family of metabolic and regulatory enzymes. *Cell Mol Life Sci* 65, 3895-906 (2008).
16. Chinen, A., Matsumoto, Y. & Kawamura, S. Reconstitution of ancestral green visual pigments of zebrafish and molecular mechanism of their spectral differentiation. *Mol Biol Evol* 22, 1001-10 (2005).
17. Dahlem, T. J. et al. Simple methods for generating and detecting locus-specific mutations induced with TALENs in the zebrafish genome. *PLoS Genet* 8, e1002861 (2012).
18. Reuter, T. E., White, R. H. & Wald, G. Rhodopsin and porphyropsin fields in the adult bullfrog retina. *J Gen Physiol* 58, 351-71 (1971).
19. Arnson, H. A., Fu, X. & Holy, T. E. Multielectrode array recordings of the vomeronasal epithelium. *J Vis Exp* (2010).
20. Szymczak-Workman, A. L., Vignali, K. M. & Vignali, D. A. Design and construction of 2A peptide-linked multicistronic vectors. *Cold Spring Harb Protoc* 2012, 199-204 (2012).
21. Busskamp, V. et al. Genetic reactivation of cone photoreceptors restores visual responses in retinitis pigmentosa. *Science* 329, 413-7 (2010).
22. Jacobs, G. H., Williams, G. A., Cahill, H. & Nathans, J. Emergence of novel color vision in mice engineered to express a human cone photopigment. *Science* 315, 1723-5 (2007).
23. Corbo, J. C., Levine, M. & Zeller, R. W. Characterization of a notochord-specific enhancer from the Brachyury promoter region of the ascidian, Ciona intestinalis. *Development* 124, 589-602 (1997).
24. Corbo, J. C., Di Gregorio, A. & Levine, M. The ascidian as a model organism in developmental and evolutionary biology. *Cell* 106, 535-8 (2001).
25. Kwasnieski, J. C., Mogno, I., Myers, C. A., Corbo, J. C. & Cohen, B. A. Complex effects of nucleotide variants in a mammalian cis-regulatory element. *Proc Natl Acad Sci USA* 109, 19498-503 (2012).
26. Montana, C. L. et al. Reprogramming of adult rod photoreceptors prevents retinal degeneration. *Proc Natl Acad Sci USA* 110, 1732-7 (2013).

Introduction to Example 4

Optogenetics is the most important technological breakthrough in neuroscience during the past decade and holds outstanding promise for the treatment of human disease[12-14]. The retina is uniquely amenable to optogenetic therapies because of its optical accessibility. Indeed, several proof-of-concept studies have been published that demonstrate the feasibility of restoring visual sensitivity to retinas devoid of rods and cones[2-4]. One therapeutic approach is to introduce optogenetic actuators into non-photosensitive inner retinal cell types (either bipolar cells or ganglion cells), thereby endowing them with visual sensitivity. Optogenetic targeting of bipolar cells is generally considered a more effective therapeutic strategy than targeting ganglion cells because the former permits a greater degree of inner retinal processing of the light signal and thus is more likely to restore realistic visual function[3-6].

Despite the enormous promise of optogenetics for vision restoration, optogenetic treatments for blindness require the application of high-intensity blue light, which has the potential to cause retinal photodamage with chronic treatment.

The present invention seeks to address this problem, by using a novel chromophore-based strategy for red-shifting the sensitivity of the optogenetic actuators, thereby minimizing photodamage. This approach will be used to treat a mouse model of retinitis pigmentosa. In summary, this work addresses major barriers to progress in translating optogenetic therapies to the clinic.

This invention includes the highly innovative strategy of chromophore substitution as a strategy for red-shifting optogenetic actuators for therapeutic purposes. The inventors have recently discovered the enzyme that fish and amphibians use to convert retinal into 3,4-didehydroretinal, thereby switching 'rhodopsin' into 'porphyropsin' to red-shift their photoreceptor sensitivities[17,18]. In a novel biomimetic approach, we will co-express this enzyme with optogenetic actuators to red-shift their sensitivities for the purpose of treating retinal degeneration.

Example 4. Restoration of Vision to Blind Mice By Targeting Red-Shifted Optogenetic Devices to ON and OFF Bipolar Optogenetics holds significant promise for restoring vision to blind patients, but current pre-clinical treatment strategies require high-intensity blue light to stimulate ChR2 and related optogenetic actuators, posing a risk of retinal photodamage[5,6,41,42]. We will use a novel strategy to red-shift the optogenetic chromophore and create sensors that can be activated by far red (>650 nm) light. This red-shifting approach will be used to restore functional vision to photoreceptor-less rd1 mutant mice.

In addition to reducing the potential for light toxicity, red-shifted optogenetic actuators offer additional advantages over blue-sensitive photoswitches. First, many blind patients are photophobic: they experience a painful sensation when exposed to bright light. Photophobia is significantly reduced at the longer wavelengths used to stimulate red-shifted actuators[42,43]. Second, blue-green light can cause pupillary constriction, an involuntary reflex mediated by the inner retinal photoreceptor, melanopsin, which is maximally sensitive to 480 nm light[5,6]. Red-shifted actuators will reduce the spectral overlap between the actuator and melanopsin, minimizing this side effect. Lastly, the human macula contains carotenoid pigments that strongly absorb blue-green light, and thus functional optogenetic rescue of macular vision could be enhanced by the use of red-shifted optogenetic devices[41,44-46]. For all of these reasons, red-shifting of optogenetic actuators would represent a promising therapeutic advance for patients with blindness caused by photoreceptor loss.

Two prior studies demonstrated the feasibility of restoring vision to blind mice by gene transfer of channelrhodopsin-2 (ChR2), to ON bipolar cells via electroporation[3] or AAV[4]. These studies were limited by inefficient bipolar targeting and expression, and required application of phototoxic levels of blue-green light to stimulate the ChR2. We aim to improve upon these results with a new strategy for red-shifting the chromophore of the optogenetic actuators. This approach promises to dramatically improve light-sensitivity in the rescued mice and avoid the retinal damage associated with high-intensity blue light exposure, permitting significant restoration of visual function to blind animals.

To impart far red light sensitivity to ON bipolar cells, we will co-express a red-shifted optogenetic actuator, ReaChR (Amax=590 nm), with the retinoid processing enzyme, Cyp27c1. Compared to published red-shifted channelrhodopsins (VChR1 and C1V1$^{E122T}$)[54,55], ReaChR has an enhanced steady-state response to long-wavelength light (>600 nm) and improved expression in mammalian cells[47]. Co-expression of a mammalian codon-optimized version of zebrafish Cyp27c1 in bipolar cells will convert retinal into 3,4-didehydroretinal in those cells. We will use the pan-bipolar promoter Chx10 to drive Cyp27c1 to generate 3,4-didehydroretinal in both ON and OFF bipolar cells. In vitro studies have demonstrated that replacing retinal with 3,4-didehydroretinal in optogenetic actuators can red-shift their action spectra by greater than 30 nm[50]. We therefore expect that co-expression of Cyp27c1 will red-shift the $A_{max}$ of ReaChR from 590 nm to ~620 nm. Based on the published action spectrum of ReaChR[47], we estimate that the 3,4-didehydroretinal-containing variant will have half-maximal sensitivity at ~670 nm, permitting optical control of the actuator with far red light.

In contrast to ON bipolar cells, which respond maximally to light onset, OFF bipolars respond to decrements in light intensity[3-5]. Accordingly, we will target OFF bipolar cells with a red-shifted optogenetic inhibitor, eNpHR3.0, (Amax=590 nm)39. Because the size of the synthetic gene circuit for OFF bipolar targeting (~4.4 Kb) approaches the maximal carrying capacity of AAV (4.7 Kb)[56], is not possible to include Cyp27c1 in this virus. However, the co-injected 'ReaChR' virus (described above) will contain the Cyp27c1 gene driven by the pan-bipolar promoter Chx10. Thus, 3,4-didehydroretinal will be generated in all bipolar cells and thus be available for use by eNpHR3.0 in the OFF bipolar cells.

AAVs containing the ON and OFF bipolar targeting constructs described above will be injected into blind rd1 mutant mice. Two week old mice will receive intravitreal injection of equal titers of each virus, and the mice will be initially evaluated for functional visual restoration at eight weeks. Intraocular injections are made at two weeks to stimulate bipolar cells before retinal remodeling or loss of bipolar cells takes place[57,58].

We will test the ability of our therapeutic approach to drive light responses in retinal ganglion cells (RGC) using multi-electrode array (MEA) recordings from retinal whole mounts. Retinas will be dissected from treated and untreated eyes and responses of RGC populations to flashes of light will be recorded. Responses of individual RGCs will also be determined by spike sorting. We will confirm that the RGC signals we measure come from light-sensitive bipolar cells by evaluating retinas in the presence of APB (which blocks photoreceptor to ON bipolar signaling) and CPP and CNQX (which block bipolar to RGC signaling)[3,4]. We will determine whether improved targeting of bipolar cells enhances absolute sensitivity over prior approaches[3,4]. We will evaluate the effects of Cyp27c1 on wavelength sensitivity by analyzing rd1 mice treated with and without Cyp27c1 co-expression. We predict that Cyp27c1 co-expression will extend sensitivity well beyond 650 nm. Initially, we will treat rd1 mice separately with the ON bipolar construct and the OFF bipolar construct. We predict that RGCs from mice treated with the ON bipolar construct will only respond to light onset and mice treated with the OFF bipolar construct will only respond to light offset. Next, we will treat animals with both constructs together and determine whether the RGCs of treated retinas have center-surround receptive fields and that both ON and OFF responses can be recorded from individual RGCs.

Mice naturally avoid brightly lit open spaces and prefer to hide in small dark spaces[60]. This preference is lost in adult rd1 mice that lack rods and cones. We will test whether bipolar-targeted treatment restores this light avoidance behavior using a light/dark box, in which mice are allowed to choose between a darkened and a lighted compartment[2,60,61]. Mice will be habituated to a testing environment composed of a plastic tub with a dark and a light compartment connected by a small opening. Mice will then be placed in the tub, allowed to explore for a total of five minutes, and the time spent in the light will be recorded. We will perform this experiment at varying light intensities to determine the threshold intensity of the response. Results will be compared to untreated controls, as well as mice treated with the ON or OFF bipolar vectors alone, to determine if expression of photoswitches in both the excitatory and inhibitory pathways results in a functional improvement beyond the excitatiory channel alone. To determine the effects of Cyp27c1 expression on wavelength sensitivity, we will also perform this test with monochromatic light of varying wavelengths on mice treated with and without Cyp27c1 co-expression.

We will test if treated mice can learn to associate a light stimulus with a reward. To do this, we will use a forced two-choice variation of the Morris water-maze (Y-maze). Mice will be trained to associate a temporal visual cue with an escape platform. The arm containing the platform will be cued with a custom-built LED array flashing at a frequency of 2 Hz. The other arm will be equipped with a matched custom-built LED panel emitting constant non-patterned light as a decoy cue. A correct trial will be counted each time a mouse is able to swim to the correct arm and reach the platform in under a minute.

We will use a related assay to test visual acuity. Mice will be trained on a Y-maze task in which the arm of the maze containing the platform will be cued with a vertical grating, and the other arm will contain with a matched cue displaying a horizontal grating, as previously demonstrated[62]. Different treatment groups will be compared to determine whether dual targeting of ON- and OFF-bipolar cells improves contrast sensitivity and the ability to recognize patterned stimuli compared to a single vector treatment.

We predict that the newly developed red-shifted optogenetic devices will generate significantly better functional restoration in treated mice than previously possible. We expect that this approach will markedly increase light sensitivity and visual acuity, translating into behaviorally relevant visual function. In addition, the use of far red light will minimize retinal photodamage and reduce pupillary constriction, permitting more light to reach the retina and thus further enhancing sensitivity.

Red-shifting the chromophore is a new and untested strategy in vivo, but published studies in vitro suggest that it will work[50]. If we fail to achieve sufficient levels of Cyp27c1 expression utilizing the Chx10 promoter, we will drive it with a strong ubiquitous promoter. If red-shifting of the chromophore is ineffective at converting retinal into 3,4-didehydroretinal in vivo, we will pursue these studies using red-shifted optogenetic actuators alone. We recently showed that expression of a genetically encoded light-gated ionotropic glutamate receptor can restore light sensitivity to rd1 retinas[59].

In conclusion, the present invention will convert bipolar cells into red-shifted optogenetic sensors for treating retinal degeneration. This approach will permit unprecedented levels of vision restoration and set the stage for future trials in human patients with end-stage photoreceptor loss.

References for Example 4

1. Bi, A. et al. Ectopic expression of a microbial-type rhodopsin restores visual responses in mice with photoreceptor degeneration. *Neuron* 50, 23-33 (2006).
2. Busskamp, V. et al. Genetic reactivation of cone photoreceptors restores visual responses in retinitis pigmentosa. *Science* 329, 413-7 (2010).
3. Lagali, P. S. et al. Light-activated channels targeted to ON bipolar cells restore visual function in retinal degeneration. *Nat Neurosci* 11, 667-75 (2008).
4. Doroudchi, M. M. et al. Virally delivered channelrhodopsin-2 safely and effectively restores visual function in multiple mouse models of blindness. *Mol Ther* 19, 1220-9 (2011).
5. Busskamp, V., Picaud, S., Sahel, J. A. & Roska, B. Optogenetic therapy for retinitis pigmentosa. *Gene Ther* 19, 169-75 (2012).
6. Sahel, J. A. & Roska, B. Gene therapy for blindness. *Annu Rev Neurosci* 36, 467-88 (2013).
7. Doroudchi, M. M. et al. Towards optogenetic sensory replacement. *Conf Proc IEEE Eng Med Biol Soc* 2011, 3139-41 (2011).
8. Vandenberghe, L. H. & Auricchio, A. Novel adeno-associated viral vectors for retinal gene therapy. *Gene Ther* 19, 162-8 (2012).
9. Surace, E. M. & Auricchio, A. Versatility of AAV vectors for retinal gene transfer. *Vision Res* 48, 353-9 (2008).
10. Kwasnieski, J. C., Mogno, I., Myers, C. A., Corbo, J. C. & Cohen, B. A. Complex effects of nucleotide variants in a mammalian cis-regulatory element. *Proc Natl Acad Sci USA* 109, 19498-503 (2012).
11. White, M. A., Myers, C. A., Corbo, J. C. & Cohen, B. A. Massively parallel in vivo enhancer assay reveals that highly local features determine the cis-regulatory function of ChIP-seq peaks. *Proc Natl Acad Sci USA* 110, 11952-7 (2013).
12. Bernstein, J. G., Garrity, P. A. & Boyden, E. S. Optogenetics and thermogenetics: technologies for controlling the activity of targeted cells within intact neural circuits. *Curr Opin Neurobiol* 22, 61-71 (2012).
13. Alford, S. C., Wu, J., Zhao, Y., Campbell, R. E. & Knopfel, T. Optogenetic reporters. *Biol Cell* 105, 14-29 (2013).
14. Zhang, F. et al. The microbial opsin family of optogenetic tools. *Cell* 147, 1446-57 (2011).
15. Dalkara, D. et al. In vivo-directed evolution of a new adeno-associated virus for therapeutic outer retinal gene delivery from the vitreous. *Sci Transl Med* 5, 189ra76 (2013).
16. Klimczak, R. R., Koerber, J. T., Dalkara, D., Flannery, J. G. & Schaffer, D. V. A novel adeno-associated viral variant for efficient and selective intravitreal transduction of rat Muller cells. *PLoS One* 4, e7467 (2009).
17. Bridges, C. D. B. The rhodopsin-porphyropsin visual system. in *Handbook of Sensory Physiology VII/1* (ed. Dartnall, H. H. A.) 417-480 (Springer-Verlag, 1972).
18. Reuter, T. E., White, R. H. & Wald, G. Rhodopsin and porphyropsin fields in the adult bullfrog retina. *J Gen Physiol* 58, 351-71 (1971).
19. Jacobson, S. G. et al. Gene therapy for leber congenital amaurosis caused by RPE65 mutations: safety and efficacy in 15 children and adults followed up to 3 years. *Arch Ophthalmol* 130, 9-24 (2012).
20. Bennett, J. et al. Stable transgene expression in rod photoreceptors after recombinant adeno-associated virus-mediated gene transfer to monkey retina. *Proc Natl Acad Sci USA* 96, 9920-5 (1999).
21. Petrs-Silva, H. et al. High-efficiency transduction of the mouse retina by tyrosine-mutant AAV serotype vectors. *Mol Ther* 17, 463-71 (2009).
22. Brustad, E. M. & Arnold, F. H. Optimizing non-natural protein function with directed evolution. *Curr Opin Chem Biol* 15, 201-10 (2011).
23. Romero, P. A. & Arnold, F. H. Exploring protein fitness landscapes by directed evolution. *Nat Rev Mol Cell Biol* 10, 866-76 (2009).
24. Koerber, J. T., Maheshri, N., Kaspar, B. K. & Schaffer, D. V. Construction of diverse adeno-associated viral libraries for directed evolution of enhanced gene delivery vehicles. *Nat Protoc* 1, 701-6 (2006).
25. Maheshri, N., Koerber, J. T., Kaspar, B. K. & Schaffer, D. V. Directed evolution of adeno-associated virus yields enhanced gene delivery vectors. *Nat Biotechnol* 24, 198-204 (2006).
26. Dalkara, D. et al. AAV mediated GDNF secretion from retinal glia slows down retinal degeneration in a rat model of retinitis pigmentosa. *Mol Ther* 19, 1602-8 (2011).
27. Byrne, L. C. et al. AAV-mediated, optogenetic ablation of Muller Glia leads to structural and functional changes in the mouse retina. *PLoS One* 8, e76075 (2013).
28. Muller, O. J. et al. Random peptide libraries displayed on adeno-associated virus to select for targeted gene therapy vectors. *Nat Biotechnol* 21, 1040-6 (2003).
29. Koerber, J. T., Jang, J. H. & Schaffer, D. V. DNA shuffling of adeno-associated virus yields functionally diverse viral progeny. *Mol Ther* 16, 1703-9 (2008).
30. Fossat, N. et al. A new GFP-tagged line reveals unexpected Otx2 protein localization in retinal photoreceptors. *BMC Dev Biol* 7, 122 (2007).
31. Corbo, J. C. et al. CRX ChIP-seq reveals the cis-regulatory architecture of mouse photoreceptors. *Genome Res* 20, 1512-25 (2010).
32. Lee, J., Myers, C. A., Williams, N., Abdelaziz, M. & Corbo, J. C. Quantitative fine-tuning of photoreceptor cis-regulatory elements through affinity modulation of transcription factor binding sites. *Gene Ther* 17, 1390-9 (2010).
33. Kim, D. S., Matsuda, T. & Cepko, C. L. A core paired-type and POU homeodomain-containing transcription factor program drives retinal bipolar cell gene expression. *J Neurosci* 28, 7748-64 (2008).
34. LeProust, E. M. et al. Synthesis of high-quality libraries of long (150mer) oligonucleotides by a novel depurination controlled process. *Nucleic Acids Res* 38, 2522-40 (2010).
35. Dhingra, A. et al. Probing neurochemical structure and function of retinal ON bipolar cells with a transgenic mouse. *J Comp Neurol* 510, 484-96 (2008).
36. Langevin, L. M. et al. Validating in utero electroporation for the rapid analysis of gene regulatory elements in the murine telencephalon. *Dev Dyn* 236, 1273-86 (2007).
37. Penaud-Budloo, M. et al. Adeno-associated virus vector genomes persist as episomal chromatin in primate muscle. *J Virol* 82, 7875-85 (2008).
38. Montana, C. L. et al. Transcriptional regulation of neural retina leucine zipper (Nrl), a photoreceptor cell fate determinant. *J Biol Chem* 286, 36921-31 (2011).

39. Tye, K. M. et al. Amygdala circuitry mediating reversible and bidirectional control of anxiety. *Nature* 471, 358-62 (2011).
40. Hayashi, S. & McMahon, A. P. Efficient recombination in diverse tissues by a tamoxifen-inducible form of Cre: a tool for temporally regulated gene activation/inactivation in the mouse. *Dev Biol* 244, 305-18 (2002).
41. Stringham, J. M. & Snodderly, D. M. Enhancing performance while avoiding damage: a contribution of macular pigment. *Invest Ophthalmol Vis Sci* 54, 6298-306 (2013).
42. Stringham, J. M., Fuld, K. & Wenzel, A. J. Action spectrum for photophobia. *J Opt Soc Am A Opt Image Sci Vis* 20, 1852-8 (2003).
43. Wenzel, A. J., Fuld, K., Stringham, J. M. & Curran-Celentano, J. Macular pigment optical density and photophobia light threshold. *Vision Res* 46, 4615-22 (2006).
44. Degenaar, P. et al. Optobionic vision—a new genetically enhanced light on retinal prosthesis. *J Neural Eng* 6, 035007 (2009).
45. Snodderly, D. M., Brown, P. K., Delori, F. C. & Auran, J. D. The macular pigment. I. Absorbance spectra, localization, and discrimination from other yellow pigments in primate retinas. *Invest Ophthalmol Vis Sci* 25, 660-73 (1984).
46. Bone, R. A., Landrum, J. T. & Tarsis, S. L. Preliminary identification of the human macular pigment. *Vision Res* 25, 1531-5 (1985).
47. Lin, J. Y., Knutsen, P. M., Muller, A., Kleinfeld, D. & Tsien, R. Y. ReaChR: a red-shifted variant of channelrhodopsin enables deep transcranial optogenetic excitation. *Nat Neurosci* 16, 1499-508 (2013).
48. Temple, S. E. et al. Seasonal cycle in vitamin A1/A2-based visual pigment composition during the life history of coho salmon (*Oncorhynchus kisutch*). *J Comp Physiol A Neuroethol Sens Neural Behav Physiol* 192, 301-13 (2006).
49. Wald, G. THE PORPHYROPSIN VISUAL SYSTEM. *J Gen Physiol* 22, 775-94 (1939).
50. Sineshchekov, O. A., Govorunova, E. G., Wang, J. & Spudich, J. L. Enhancement of the long-wavelength sensitivity of optogenetic microbial rhodopsins by 3,4-dehydroretinal. *Biochemistry* 51, 4499-506 (2012).
51. Allison, W. T., Haimberger, T. J., Hawryshyn, C. W. & Temple, S. E. Visual pigment composition in zebrafish: Evidence for a rhodopsin-porphyropsin interchange system. *Vis Neurosci* 21, 945-52 (2004).
52. Coon, M. J. Cytochrome P450: nature's most versatile biological catalyst. *Annu Rev Pharmacol Toxicol* 45, 1-25 (2005).
53. Nelson, D. R. et al. P450 superfamily: update on new sequences, gene mapping, accession numbers and nomenclature. *Pharmacogenetics* 6, 1-42 (1996).
54. Zhang, F. et al. Red-shifted optogenetic excitation: a tool for fast neural control derived from Volvox carteri. *Nat Neurosci* 11, 631-3 (2008).
55. Yizhar, O. et al. Neocortical excitation/inhibition balance in information processing and social dysfunction. *Nature* 477, 171-8 (2011).
56. Grieger, J. C. & Samulski, R. J. Packaging capacity of adeno-associated virus serotypes: impact of larger genomes on infectivity and postentry steps. *J Virol* 79, 9933-44 (2005).
57. Strettoi, E. & Pignatelli, V. Modifications of retinal neurons in a mouse model of retinitis pigmentosa. *Proc Natl Acad Sci USA* 97, 11020-5. (2000).
58. Strettoi, E., Pignatelli, V., Rossi, C., Porciatti, V. & Falsini, B. Remodeling of second-order neurons in the retina of rd/rd mutant mice. *Vision Res* 43, 867-77 (2003).
59. Caporale, N. et al. LiGluR restores visual responses in rodent models of inherited blindness. *Mol Ther* 19, 1212-9 (2011).
60. Bourin, M. & Hascoet, M. The mouse light/dark box test. *Eur J Pharmacol* 463, 55-65 (2003).
61. Lin, B., Koizumi, A., Tanaka, N., Panda, S. & Masland, R. H. Restoration of visual function in retinal degeneration mice by ectopic expression of melanopsin. *Proc Natl Acad Sci USA* 105, 16009-14 (2008).
62. Wong, A. A. & Brown, R. E. Visual detection, pattern discrimination and visual acuity in 14 strains of mice. *Genes Brain Behav* 5, 389-403 (2006).

What is claimed is:

1. A composition comprising a vector, the vector comprising a polynucleotide sequence encoding a polypeptide, the polypeptide comprising at least one optogenetic device and a retinoid processing enzyme.

2. The composition of claim 1, wherein the polypeptide comprises a proteolytic cleavage site between the optogenetic device and the retinoid processing enzyme.

3. The composition of claim 1, wherein the optogenetic device comprises an optogenetic activator.

4. The composition of claim 3, wherein the optogenetic activator is ReaChR.

5. The composition of claim 1, wherein the retinoid processing enzyme is a retinal 3,4-dehydrogenase.

6. The composition of claim 5, wherein the retinoid processing enzyme is Cyp27c1.

* * * * *